(12) United States Patent
Chen et al.

(10) Patent No.: US 7,763,268 B2
(45) Date of Patent: Jul. 27, 2010

(54) LOAD BEARING HYDROGEL IMPLANTS

(75) Inventors: Weiliam Chen, Mount Sinai, NY (US); Lihui Weng, Ames, IA (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/355,577

(22) Filed: Jan. 16, 2009

(65) Prior Publication Data

US 2010/0029789 A1 Feb. 4, 2010

Related U.S. Application Data

(60) Provisional application No. 61/022,254, filed on Jan. 18, 2008.

(51) Int. Cl.
*A61F 13/00* (2006.01)
*A61F 7/00* (2006.01)
*A61K 9/14* (2006.01)
*A61K 9/50* (2006.01)

(52) U.S. Cl. .................. 424/422; 424/423; 424/434; 424/487; 424/501; 524/916

(58) Field of Classification Search ............. 424/422, 424/423, 434, 487, 501; 524/916
See application file for complete search history.

(56) References Cited

U.S. PATENT DOCUMENTS

| | | | |
|---|---|---|---|
| 4,573,448 A | 3/1986 | Kambin | |
| 4,582,865 A | 4/1986 | Balazs et al. | |
| 5,015,255 A | 5/1991 | Kuslich | |
| 5,313,962 A | 5/1994 | Obenchain | |
| 5,383,884 A | 1/1995 | Summers | |
| 5,464,932 A * | 11/1995 | Allcock et al. | 528/399 |
| 5,702,454 A | 12/1997 | Baumgartner | |
| 5,762,629 A | 6/1998 | Kambin | |
| 5,976,146 A | 11/1999 | Ogawa et al. | |
| 5,976,186 A | 11/1999 | Bao et al. | |
| 6,095,149 A | 8/2000 | Sharkey et al. | |
| 6,127,597 A | 10/2000 | Beyar et al. | |
| 6,174,645 B1 * | 1/2001 | Russell et al. | 430/286.1 |
| 6,190,603 B1 * | 2/2001 | Steinmann et al. | 264/496 |
| 7,014,633 B2 | 3/2006 | Cragg | |
| 7,045,366 B2 * | 5/2006 | Huang et al. | 436/529 |
| 7,204,851 B2 | 4/2007 | Trieu et al. | |

OTHER PUBLICATIONS

Abraham et al., Hydrophilic hybrid IPNs of segmented polyurethanes and copolymers of vinylpyrrolidone for applications in medicine, Biomaterials, 22:1971-85 (2001).
Bono and Garfin, History and Evolution of Disc Replacement, The Spine Journal, 4:145S-150S (2004).
Boucard et al., The use of physical hydrogels of chitosan for skin regeneration following third-degree burns, Biomaterials, 28:3478-88 (2007).
Bulpitt and Aeschliman, New strategy for chemical modification of hyaluronic acid: preparation of functionalized derivatives and their use in the formation of novel biocompatible hydrogels, J. Biomed. Mater. Res., 47:152-69 (1999).
Burdick et al., Controlled degradation and mechanical behavior of photopolymerized hyaluronic acid networks, Biomacromolecules, 6:386-91 (2005).
Chang et al., Tissue engineering-based cartilage repair with allogenous chondrocytes and gelatinechondroitinehyaluronan tri-co-polymer scaffold: a porcine model assessed at 18, 24, and 36 weeks, Biomaterials, 27:1876-88 (2006).
Drury and Mooney, Hydrogels for tissue engineering: scaffold design variables and applications, Biomaterials, 24:4337-51 (2003).
Gong et al., Double network hydrogels with extremely high mechanical strength, Adv. Mater., 15:1155-8 (2003).
Haraguchi et al., Compositional effects on mechanical properties of nanocomposite hydrogels composed of poly (N,N-dimethylacrylamide) and clay, Macromolecules, 36:5732-41 (2003).
Hornebeck et al., Down-Regulation of tissue inhibitor of matrix metalloprotease-4 (TIMP-1) in aged human skin contributes to matrix degradation and impaired cell growth and survival, Pathol. Biol., 51:569-573 (2003).
Jia et al., Prolongation of sciatic nerve blockade by in situ cross-linked hyaluronic acid, Biomaterials, 25(19):4797-4804 (2004).
Joddar et al., Elastogenic Effects of exogenous hyaluronan oligosaccharides on vascular smooth muscle cells, Biomaterials, 27:2994-3004 (2006).
Leach et al., Development of photocrosslinkable hyaluronic acid-polyethylene glycol-peptide composite hydrogels for soft tissue engineering, J. Biomed. Mater. Res. A., 1:74-82 (2004).
Liu et al., Disulfide-crosslinked hyaluronan-gelatin sponge: Growth of fibrous tissue invivo, J. Biomed. Mater. Res. A, 68:142-149 (2004).
Liu et al., an osteoconductive collagen/hyaluronate matrix for bone regeneration, Biomaterials, 20:1097-1108 (1999).
Koneko D et al., Mechanically strong hydrogels with ultra-low frictional coefficients, Adv. Mater., 17:535-8 (2005).
Nettles et al., Photocrosslinkable hyaluronan as a scaffold for articular cartilage repair, Ann. Biomed. Eng., 32:391-397 (2004).
Park et al., Photopolymerized hyaluronic acid-based hydrogels and interpenetrating networks, Biomaterials, 24:893-900 (2003).
Park et al., Biological characterization of EDC crosslinked collagen hyaluronic acid matrix in dermal tissue restoration, Biomaterials, 24:1631-41 (2003).
Ramamurthi and Vesely, Smooth muscle cell adhesion on crosslinked hyaluronan gels, J. Biomed. Mater. Res., 60:196-205 (2002).
Ramamurthi et al., Ultraviolet light-induced modification of crosslinked hyaluronan gels, J. Biomed. Mater. Res. A, 66:317-329 (2003).
Rokhade et al., Novel interpenetrating polymer network microspheres of chitosan and methylcellulose for controlled release of theophylline, Carbohydr. Polym., 69:678-87 (2007).

(Continued)

*Primary Examiner*—Raymond J Henley, III
(74) *Attorney, Agent, or Firm*—Fish & Richardson P.C.

(57) ABSTRACT

The present invention features dual network hydrogels that possess the structural, mechanical, and biological properties required of load bearing three-dimensional support structures.

28 Claims, 9 Drawing Sheets

OTHER PUBLICATIONS

Segura et al., Crosslinked hyaluronic acid hydrogels: a strategy to functionalize and pattern, Biomaterials, 26:359-371 (2005).

Sodian et al. Fabrication of a trileaflet heart valve scaffold from a polyhydroxyalkanoate biopolyester for use in tissue engineering, Tissue Eng., 6:183-8 (2000).

Shu et al., Disulfide-crosslinked hyaluronan-gelatin hydrogel films: a covalent mimic of the extracellular matrix for in vitro cell growth, Biomaterials, 24:3825-34 (2003).

Tamada et al., Fibroblast growth on polymer surfaces and biosynthesis of collagen, J. Biomed. Mater. Res., 28:783-789 (1994).

Tomihata and Ikada, Crosslinking of hyaluronic acid with glutaraldehyde. J Polym. Sci. Part A, Polym Chem., 35:3553-9 (1997).

Whittaker et al., Basic Res. Cardiol., 89:397-410 (1994).

Van der Valk et al., Interaction of fibroblasts and polymer surfaces: relationship between surface free energy and fibroblast spreading, J. Biomed. Res., 17:807-817 (1983).

Yeo Y et al., Peritoneal adhesion prevention with an in situ cross-linkable hyaluronan gel containing tissue-type plasminogen activator in a rabbit repeated-injury model, Biomaterials, 28:3704-13 (2007).

* cited by examiner

LOAD BEARING HYDROGEL IMPLANTS

CLAIM OF PRIORITY

This application claims the benefit of U.S. Provisional Patent Application No. 61/022,254, filed on Jan. 18, 2008, the entire contents of which is hereby incorporated by reference.

STATEMENT REGARDING FEDERALLY SPONSORED RESEARCH OR DEVELOPMENT

This invention was made with government support under grant number DK068401 awarded by the National Institutes of Health. The government has certain rights in the invention.

TECHNICAL FIELD

This invention relates to compositions and methods for treating a spinal disorder in a subject. More particularly, this invention relates to hyaluronan-based hydrogels for use as load bearing orthopaedic implants and/or spinal disc substitutes.

SUMMARY OF THE INVENTION

Four out of five people will experience a spinal disorder in their lifetime. Such disorders affect individuals of all ages, frequently resulting in disabling acute or chronic pain. Americans alone spend at least $50 billion each year on treatments for lower back pain. In many cases, treatment may be in the form of an orthopaedic implant. Currently, however, the materials available for use as implants are of a limited availability (e.g., cortical bone) or lack the required biological and/or structural properties (Bono and Garfin, *The Spine Journal*, 4:145S-150S, 2004).

Hyaluronan (HA) is an abundantly available biomaterial that is currently used in a number of clinical applications due to its unique biological and viscoelastic properties. Such applications include, for example, ocular surgery, viscosupplementation (e.g., for arthritis), wound healing, and plastic surgery. Modified HA has also been used in the production of hydrogels. The modifications used to generate such HA based hydrogels involve techniques that crosslink and/or derivatize HA via its carboxylic and hydroxyl groups using, for example, dihydrazide (Yeo et al., *Biomaterials*, 28:3704-3713, 2007; Jia et al., *Biomaterials*, 25:4797-4804, 2004), carbodiimides (Park et al., *Biomaterials*, 24:1631-1641, 2003; Chang et al., *Biomaterials*, 27:1876-1788, 2006), dialdehyde (Tomihata et al., *J. Polym. Sci.: Part A: Polym. Chem.*, 35:3553-3559, 1997; Bulpitt et al., *J. Biomed. Mater. Res.*, 47:152-169, 1999), disulfide (Shu et al., *Biomaterials*, 24:3825-3834, 2003; Liu et al., *J. Biomed. Mater. Res. A.*, 68:142-149, 2004), and a variety of other agents (Segura et al., *Biomaterials*, 26:359-371, 2005; Balazs et al., U.S. Pat. No. 4,582,865, 1986; Dulong et al., *Carbohydr. Polym.*, 57:1-6, 2004; Ramamurthi et al., *J. Biomed. Mater. Res. A.*, 66:317-329, 2003; Burdick et al., *Biomacromolecules*, 6:386-391, 2005). The use of HA based hydrogels as biomaterials has been complicated, however, by low biocompatibility and/or low mechanical strength. In addition, many of these hydrogels are biodegradable or deteriorate over time, limiting their potential application as long-term implants.

While biodegradable hydrogels formulated from photocrosslinking glycidyl methacrylate (GMA) derivatized HA (MeHA) have good biocompatibility (Leach et al., *Biotech. Bioeng.*, 82:578-589, 2003; Nettles et al., *Ann. Biomed. Eng.*, 32:391-397, 2004), they are extremely brittle and, therefore, lack structural integrity and mechanical strength. This limits their potential use in many biomedical fields where good mechanical properties are required. For example, they cannot be used as load bearing implants.

We have developed a biomedical material that is both biocompatible and strong enough for use as a load bearing implant. The present invention is based, at least in part, on the discovery that HA-based double (or dual) network hydrogels possess the structural, mechanical, and biological properties required for load bearing implants.

Accordingly, the invention features a hydrogel comprising (a) a first network comprising photocrosslinkable hyaluronan and (b) a second network comprising a hydrophillic polymer or a monomer thereof, wherein (a) and (b) are combined and crosslinked (e.g., photocrosslinked). The networks can be prepared individually and then combined or made and combined in the same step. The network is a highly ramified macromolecule in which essentially each constitutional unit is connected to each other constitutional unit and to the macroscopic phase boundary by many permanent paths through the macromolecule, the number of such paths increasing with the average number of intervening bonds. The network can be interpenetrating or semi-interpenetrating.

The hydrogels can include photocrosslinkable hyaluronan that comprises hyaluronan derivatized with glycidyl methacrylate and may further include a crosslinker (e.g., an acrylamide such as N,N'-methylene bisacrylamide (MBAAm)) and/or a photoinitiator.

The hydrophilic polymer can be a synthetic polymer (e.g., an acrylamide such as poly(N,N-dimethylacrylamide) (PDMAAm) or a monomer thereof; 2-N-Acetyl-β-D-glucosamine polyacrylamide biotin or a monomer thereof, α-D-6-O-Phosphomannopyranoside polyacrylamide biotin or a monomer thereof, α-D-Mannopyranoside polyacrylamide biotin or a monomer thereof, aldolase-polyacrylamide or a monomer thereof, biotin-2-N-acetyl-α-D-galactosamine polyacrylamide or a monomer thereof, biotin-α-D-galactopyranoside polyacrylamide or a monomer thereof, biotin-α-D-glucopyranoside polyacrylamide or a monomer thereof, biotin-α-D-N-acetylneuraminide polyacrylamide or a monomer thereof, biotin-β-D-galactopyranoside polyacrylamide or a monomer thereof, biotin-β-D-glucopyranoside polyacrylamide or a monomer thereof, fluorescein-α-D-galactosamine polyacrylamide or a monomer thereof, fluorescein-α-D-mannopyranoside-polyacrylamide or a monomer thereof, fluorescein α-D-N-acetylneuraminide-polyacrylamide or a monomer thereof, fluorescein-β-D-galactopyranoside polyacrylamide or a monomer thereof, fluorescein-β-D-glucopyranoside polyacrylamide or a monomer thereof, fluorescein-β-D-N-acetylgalactosamine polyacrylamide or a monomer thereof, lacto-N-biose polyacrylamide biotin or a monomer thereof, Enzacryl® AA, N,N-dimethylacrylamide or a monomer thereof, poly[N-(1-naphthyl)-N-phenylacrylamide] or a monomer thereof, poly[N-(1-naphthyl)-N-phenylmethacrylamide or a monomer thereof, and 1-[N-[Poly(3-allyloxy-2-hydroxypropyl)]-2-aminoethyl]-2-imidazolidinone or a monomer thereof.

The hydrophilic polymer can be an organic polymer, and the hydrogels can comprise 0-99% water. The hydrogel can be lyophilized; the hydrogel can have a compressive modulus over about 0.4 MPa and less than about 10 MPa; the hydrogel can have a fracture strength of more than about 5.2 MPa and less than about 800 MPa. The crosslinking density of the second network can be lower than the crosslinking density of the first network, and the second network can be present at about 1-5 mol/L. The hydrogel can be biocompatible and resistant to biodegradation and can further include a cell (e.g., a fibroblast or stem cell) or a component of the extracellular matrix. Alternatively, or in addition, the hydrogel can include a pharmaceutical agent.

The invention also features medical devices that include the hydrogels described herein. The device can be a spinal support device, an artificial vertebral disc, or a spinal prosthesis.

The hydrogels and medical devices can be used to treat a spinal injury or disorder. To carry out the method, one can identify a patient in need of treatment; and administer to the patient a hydrogel or medical device as described herein. The spinal injury or disorder can be a ruptured or injured intervertebral disc or a degenerative disk disease. As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the methods of the present invention. We may use the terms "patient," "subject," and "individual" interchangeably to refer to a vertebrate, and more particularly to a mammal. While the methods are clearly intended for the treatment of humans, they can also be applied to farm animals, show animals, laboratory animals, pets, and the like.

Methods of making dual network hydrogels can be carried out by: (a) providing a photocrosslinked first network comprising hyaluronan; (b) providing a second network comprising a organic or synthetic polymer; and (c) photocrosslinking the first network and the second network to obtain the dual network hydrogel. The photocrosslinked first network can be obtained by preparing a solution of hyaluronan in water; adding to the solution triethylamine, tetrabutylammonium bromide and glycidyl methacrylate; dialyzing the solution; lyophilizing the solution; an irradiating the solution in the presence of a photoinitiator (e.g., 2-oxo-ketoglutaric acid). The finished hydrogels can also be dialyzed to improve their purity.

Photocrosslinking the first network and the second network can be achieved by contacting the first network with a hydrophilic polymer or a monomer thereof in the presence of a crosslinking agent and a photoinitiator to create a mixture and subsequently irradiating the mixture.

Kits including the present reagents for making hydrogels; the hydrogels per se, and devices fashioned from the hydrogels are also within the scope of the present invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 9A, 9C, and 9E show the surfaces of hydrogels cultured without cells. FIGS. 9B, 9D, and 9F show the surfaces of hydrogels co-cultured with cells for 1 month. Scale is 100 μm.

DETAILED DESCRIPTION

Figures 1A, 1B:
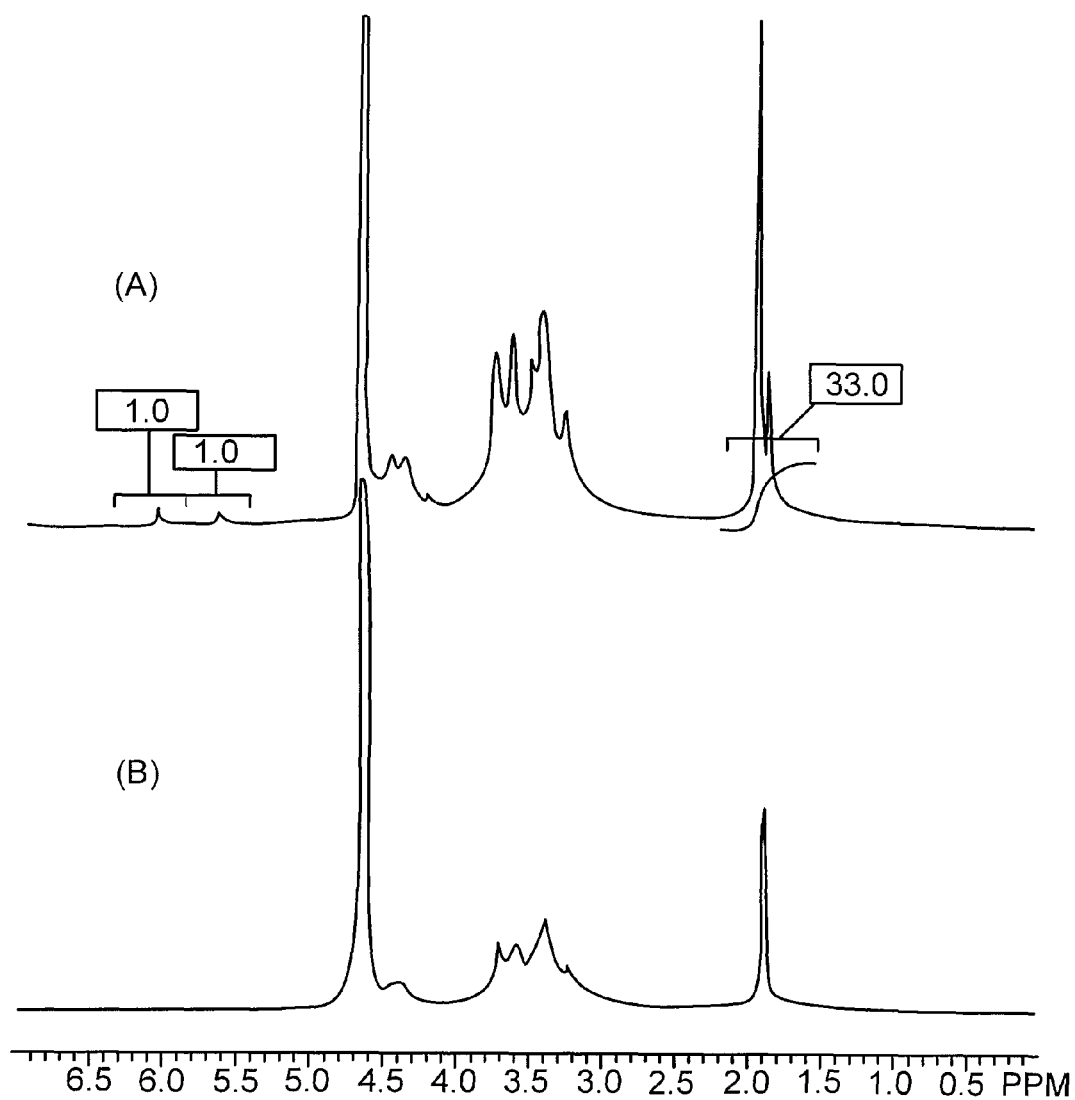
FIGS. 1A and 1B are line graphs showing $^1H$ NMR spectra of modified photocrosslinkable HA (A) and unmodified HA (B). The integrals in the boxes at 5.6, 6.1 and 1.9 ppm were 1.0, 1.0, and 33.0, respectively.

We have made HA-based hydrogels that include at least two networks having non-identical properties. For example, the first network can be stiff and/or brittle and can be crosslinked (e.g., photocrosslinked) with a second network that is soft and/or ductile. The multi- or dual network hydrogel then has properties that are non-identical to those of the individual networks alone. For example, while the first network alone may be too brittle for use as a load bearing implant and the second network may be too soft, the two networks, when combined to form the present hydrogels, possess the structural, mechanical, and biological characteristics required for a load bearing implant. For example, the double or dual network HA hydrogels can have an internal structure with desirable swelling properties and structural and mechanical properties suitable for long-term use. For example, the implants can be highly resistant to biodegradation. They may also be compatible with cell growth and extracellular matrix (ECM) formation.

The precise mechanical properties of the hydrogel or a device fashioned therefrom can be altered by varying the ratio of the polymer in the first network (e.g., hyaluronan) to that of the polymer in the second network (e.g., polyacrylamide). Alternatively, or in addition, one can vary the crosslinking densities. Even hydrogels containing as much as about 90% water are rigid enough to support loads (e.g., to support the vertebral column) while being resilient to compressive forces. Our hydrogels show a non-linear behavior with increasing deformation at least with respect to a compression force.

Hyaluronan (HA): HA, which is also referred to as hyaluronic acid or hyaluronate, is a naturally occurring, high molecular weight, non-sulfated glycosaminoglycan synthesized in the plasma membrane of fibroblasts and other cells. HA is one of several glycosaminoglycans that are widely distributed around the body and is a universal component of the ECM (Shu et al., *Biomaterials*, 24:3825-3834, 2003). As such, HA plays important and well documented roles in various biological processes, such as cell proliferation, cell growth, and wound healing (Joddar et al., *Biomaterials*, 27:2994-3004, 2006).

Our interest in HA and other glycosaminoglycans as biomaterials is due to their structural, chemical, and biological properties. HA is a linear polysaccharide composed of repeating disaccharides, which themselves are composed of D-glucuronic acid and D-N-acetylglucosamine, linked together by alternating β-1, 4 and β-1, 3 glycosidic bonds. The structure of HA is homologous in all species, and it is immunologically inert. Polymers of HA can range in size from about $1\times10^5$ to $5\times10^6$ Daltons. Larger polymers can be enzymatically digested using hyaluronidase to obtain HA polymers with lower molecular weights. Generally, however, HA polymers are useful in various applications, including the preparation of hydrogels and double network hydrogels described herein, irrespective of their molecular weight.

HA is available commercially from a number of manufacturers. The most commonly used forms are sodium HA and a non-animal stabilized hyaluronic acid (NASHA), which can be produced by bacterial fermentation from streptococci bacteria. As NASHA is derived from a non-animal source, its use further reduces the risk of immunogenicity and disease transmission. Either HA, sodium HA, NASHA or combinations thereof can be used in the present hydrogels.

Hydrogels: Hydrogels are multifunctional, three-dimensional crosslinked polymeric materials with unique physiochemical and mechanical properties. These properties can be modulated by varying the crosslinking density and material combinations within the hydrogel (Drury et al., *Biomaterials*, 24:4337-4351, 2003). Generally, hydrogels are highly porous biomaterials that permit gas and nutrient exchange, which can facilitate long-term survival of any cells present.

Double (or Dual) Network Hydrogels: Commercially available HA can be modified to increase its adhesive properties and crosslinked to increase its stability and form hydrogels (Liu et al., *Biomaterials*, 20:1097-1080, 1997; Yeo et al., *Biomaterials*, 28:3704-3713, 2007; Jia et al., *Biomaterials*, 25:4797-4804, 2004; Park et al., *Biomaterials*, 24:1631-1641, 2003; Chang et al., *Biomaterials*, 27:1876-1788, 2006; Tomihata et al., *J. Polym. Sci.: Part A: Polym. Chem.*, 35:3553-3559, 1997; Bulpitt et al., *J. Biomed. Mater. Res.*, 47:152-169, 1999; Shu et al., *Biomaterials*, 24:3825-3834, 2003; Liu et al., *J. Biomed. Mater. Res. A.*, 68:142-149, 2004; Segura et al., *Biomaterials*, 26:359-371, 2005; Balazs et al., U.S. Pat. No. 4,582,865, 1986; Dulong et al., *Carbohydr. Polym.*, 57:1-6, 2004; Ramamurthi et al., *J. Biomed. Mater. Res. A.*, 66:317-329, 2003; Burdick et al., *Biomacromolecules*, 6:386-391, 2005; Leach et al., *Biotech. Bioeng.*, 82:578-589, 2003; Nettles et al., *Ann. Biomed. Eng.*, 32:391-397, 2004). Chemical crosslinking results in polymeric networks formed through covalent interactions while physical crosslinking results in polymeric networks formed through non-covalent interactions.

The present multi- or double (dual) network hydrogels include at least first and second polymeric networks. In one embodiment, the first network can be one that, alone, has stiff and brittle structural properties and the second network can be one that, alone, has soft and ductile properties (i.e., is softer and/or more ductile than the first network).

If required, one or more of the following parameters may be used to identify a stiff and brittle polymer network suitable for incorporation as the first network and a soft and ductile polymer network suitable for incorporation as the second network. For example, to identify or distinguish between the two networks, one can consider the extent of crosslinking (a stiff and brittle network will be more highly crosslinked (more densely crosslinked) than a soft and ductile network).

For example, a stiff and brittle network suitable for incorporation as the first network may have a fracture stress threshold that is at least or about 0.1× to 10× higher than a soft and ductile network, (e.g., at least or about 0.1×; 0.5×; 1×; 2×; 3×; 5×; or 10× or more). With respect to fracture strain, a stiff and brittle network may have a fracture strain threshold that is 0.1% to 99% lower than a soft and ductile network (e.g., 0.1%; 1%; 2%; 5%; 10%; 20%; 25%; 30%; 50%; 60%; 70%; 80%; 90%; 95%; or 99% lower).

As noted above, we have found that when a first network that has stiff and brittle structural properties is crosslinked with a second network that has soft and ductile properties, a double network hydrogel is formed that has structural, mechanical, and biological properties that are favorable for use as a load bearing, implantable biomaterial.

The first network can contain at least HA, for example, photocrosslinkable HA, and the second network can contain at least a polymer (e.g., a hydrophilic organic or synthetic polymer) that is crosslinked with the first network. Photocrosslinkable HA may be produced by derivatizing HA with glycidyl methacrylate (GMA) to produce a modified methyacrylated HA. The amount of methyacrylated HA may be assessed using $^1$H-NMR, where peaks at about 5.6 and/or about 6.1 ppm on a $^1$H-NMR spectra indicate that HA has been successfully GMA-derivatized and is photocrosslinkable. The percentage methylation of HA may be determined by integrating the methyl peak observed at 1.9 ppm with the acrylic double bond peaks at about 5.6 and about 6.1 ppm. A sample of photocrosslinkable HA may contain at least 1% methyacrylated HA (i.e., relative to the total amount of HA in the same sample; e.g., at least or about 1%, 2%, 3%, 4%, 5%, 6%, 7%, 8%, 9% or 10%). In addition to HA and GMA, the reaction may also include triethylamine (TEA) and tetrabutylammonium (TBAB), the amounts of which may be adjusted to obtain at least 1% methyacrylated HA in a sample, as assessed with $^1$H-NMR.

Photocrosslinkable HA macromers undergo free radical polymerization to form three-dimensional crosslinked hydrogels containing covalent interactions when exposed to ultraviolet (UV) light (Leach et al., *Biotech Bioeng.*, 82:578-589, 2003). Here, a sample of photocrosslinkable HA containing at least 1% methyacrylated HA can be photocrosslinked by irradiating the sample with UV light between 100-400 nm (e.g., 365 nm) for a period of time sufficient to allow crosslinking (e.g., about 30 minutes to 5 hours (e.g., 2 hours)). The photocrosslinking reaction may include a photoinitiator (i.e., a compound that produces reactive species when exposed to light, (e.g., UV light)). Suitable photoinitiators include UV photoinitiators such as type I photoinitiators (e.g., benzion ethers, benzyl ketals, α-dialkoxy-aceto-phenones, α-hydroxy-alkyl-phenones, α-amino alkyl-phenones, and acyl-phosphine oxides) and type II photoinitiators (e.g., benzo-phenones/amines and thio-xanthones/amines). The photoinitiator may be 2-oxo-ketoglutaric acid. In some embodiments, the pH of the photocrosslinking reaction may be about pH 5 to pH 9 (e.g., pH 5-8, pH 5-7, or pH 7-8). The pH is not critical; the reactant can polymerize at the physiological pH of 7.4. The cross-linking can occur at room temperature (e.g., 22° C.), but can also be performed at about 20°-37° C. The resulting hydrogel is designated a PHA hydrogel. In some embodiments, a PHA hydrogel may be free of contaminants (e.g., 20%, 30%, 40%, 50%, 60%, 70%, 80%, 90%, 95%, 98%, 99%, or 100% free of contaminants) and/or may be frozen or lyophilized. Frozen and lyophilized formulations are within the scope of the present invention.

A PHA hydrogel may then be combined with a second network. It will be understood that the amount or concentration of PHA hydrogel present in a double network hydrogel may vary depending on the molecular weight of the modified HA. For example, PHA hydrogel may be present in a solution at a concentration of about 1%-3%, 1-2.8%, 1-2.5%, 1-2%, 1-1.5%, or 1-1.5% (weight/volume). In some embodiments, the PHA hydrogel may be present in a solution at a concentration of 2% (weight/volume).

In some embodiments, the second network comprises a hydrophilic organic or synthetic polymer. For example, the synthetic polymer can be an acrylamide such as 2-N-acetyl-β-D-glucosamine polyacrylamide biotin, α-D-6-O-phosphomannopyranoside polyacrylamide biotin, α-D-mannopyranoside polyacrylamide biotin, aldolase-polyacrylamide, biotin-2-N-acetyl-α-D-galactosamine polyacrylamide, biotin-α-D-galactopyranoside polyacrylamide, biotin-α-D-glucopyranoside polyacrylamide, biotin-α-D-N-acetylneuraminide polyacrylamide, galactopyranoside polyacrylamide, biotin-β-D-glucopyranoside polyacrylamide, fluorescein-α-D-galactosamine polyacrylamide, fluorescein-α-D-mannopyranoside-polyacrylamide, fluorescein α-D-N-acetylneuraminide-polyacrylamide, fluorescein-β-D-galactopyranoside polyacrylamide, fluorescein-β-D-glucopyranoside polyacrylamide, fluorescein-β-D-N-acetylgalactosamine polyacrylamide, lacto-N-biose polyacrylamide biotin, Enzacryl® AA, N,N-dimethylacrylamide, poly[N-(1-naphthyl)-N-phenylacrylamide], poly[N-(1-naphthyl)-N-phenylmethacrylamide, 1-[N-[Poly(3-allyloxy-2-hydroxypropyl)]-2-aminoethyl]-2-imidazolidinone solution, and poly(N,N-dimethylacrylamide) (PDAAm). The polymers of the second network can vary in length, and monomers can be incorporated as well. For example, the second network can include the monomer N,N-dimethylacrylamide (DAAm).

The second network may additionally include a crosslinking agent and a photoinitiator. Suitable crosslinking agents include N,N'-methylene bisacrylamide (MBAAm), dimethyl glycolacrylate, and divinylbenzene. Suitable photoinitiators include UV photoinitiators selected from the group consisting of type I photoinitiators (e.g., benzion ethers, benzyl ketals, α-dialkoxy-aceto-phenones, α-hydroxy-alkyl-phenones, α-amino alkyl-phenones, and acyl-phosphine oxides) and type II photoinitiators (e.g., benzo-phenones/amines and thio-xanthones/amines). In some embodiments, the photoinitiator may be 2-oxo-ketoglutaric acid. In some embodiments, the monomer, for example, a DAAm monomer, may be present in a solution at a concentration of about 1-5 mol/L, e.g., 1, 2, 3, 4, and 5 mol/L. In some embodiments, the monomer, e.g., a DAAm monomer, may be present in a solution at a concentration of at least or about 3 mol/L. In some embodiments, the crosslinker, for example, MBAAm, may be present in a solution at a concentration of about 0-2 mol-%, with respect to the concentration of DAAm in the solution, for example, 0, 0.01, 0.05, 0.1, 0.5, 1, and 2 mol-%. A photoinitiator (e.g., 2-oxo-ketoglutaric acid), may be present in a solution at a concentration of 0.1 mol. A double network hydrogel may then be generated by photocrosslinking the first and second network by irradiating the sample with UV light between 100-400 nm (e.g., 365 nm) for about two hours. In some embodiments, the pH of the photocrosslinking reaction may be about pH 5 to pH 9, pH 5-8, pH 5-7, and pH 5-6, e.g., pH 7.4. In some embodiments, the temperature used to perform this reaction may be room temperature (e.g., 22° C.), but it can also be performed at about 20°-37° C.

In some embodiments, a double network hydrogel may be free of contaminants (e.g., 20%, 30%, 40%, 50%, 60%, 70%, 80%, 90%, 95%, 98%, 99%, or 100% free of contaminants). In some embodiments, a double network hydrogel may be lyophilized. In some embodiments, a double network hydrogel may contain components in addition to the first and second network. For example, a double network hydrogel may contain a photoinitiator, or a crosslinking agent, or both. Some crosslinkers or unreacted monomers may remain (i.e., they may not be totally washed out during the production). In addition to water, and in some embodiments, a double network hydrogel may include minerals.

The present invention also provides methods for making a double network hydrogel. In some embodiments, the methods include methods for making double network hydrogels with PHA concentrations of 2% (w/v), DAAm concentrations of 1-5 mol/L (e.g., 1, 2, 3, 4, and 5 mol/L), and crosslinker concentrations of 0-2 mol-% (e.g., 0, 0.01, 0.05, 0.1, 0.5, 1, and 2 mol-%). In some embodiments, the methods include methods for making a double network hydrogel with a DAAm concentration of 3 mol/L and a crosslinker concentration of 0.1%. In some embodiments, the methods include methods for making a double network hydrogel with a DAAm concentration of 3 mol/L and a crosslinker concentration of 0.05 mol-%.

In some embodiments, the methods include methods to improve cell adhesion to the double network hydrogel. Such methods include increasing the surface roughness of the double network hydrogel by cutting or shearing the double network hydrogel. Additional methods include methods for increasing cell adhesion as described by Liu (Liu et al., *Biomaterials*, 20:1097-1080, 1999), which is hereby incorporated by reference.

Additional Characteristics: The structural, mechanical, and biological properties of the present hydrogels may be additionally characterized as follows.

Structurally, the hydrogels can have a pore size or average pore size less than about 50 μm (e.g., a pore size of about 1-5; 6-10; 11-15; 16-20; 21-25; 26-30; 31-35; 36-40; 41-45; or 46-49 μm. The water content can vary, and the hydrogels can have an equilibrium water content (EWC) of 70-99% (e.g., 70-95%; 70-90%; or 80-90% water).

The pore size can be determined using scanning electronic microscopy (SEM), as follows. Briefly, hydrogels should be snap frozen in a glass container using liquid nitrogen and lyophilized. Fractured pieces of hydrogel, for example, with a size of about 5 mm×2 mm×3 mm should then be mounted onto an aluminum board with copper tapes and coated with gold by plasma vapor deposition. Surface and cross-sections of the hydrogel may then be examined using, for example, a field-emission scanning electron microscope (SFEG Leo 1550, AMO GmbH, Aachen, Germany) at 20 kV.

Mechanically, the hydrogel can have:

(1) A initial compressive modulus greater than about 0.1 MPa, (e.g., 0.1-1.0; 0.1-0.8; 0.1-0.7; 0.1-0.6; 0.1-0.5; 0.1-0.4; 0.1-0.3; or 0.1-0.2 MPa).

(2) A fracture stress greater than about 0.5 MPa (e.g., greater than 1; 2; 3; 4; or 5 MPa, irrespective of the hydrogel's EWC).

(3) A fracture strain greater than about 80% (e.g., greater than 85; 90; 93; 95; or 98%).

(4) A fracture stress of greater than about 1 MPa with an EWC of greater than 80%.

The mechanical properties of the hydrogel can be determined using, for example, a MTS mechanical tester (e.g., Model 1K-16 Universal Materials Tester, Interactive Instruments, USA), as follows. Briefly, a cylindrical hydrogel specimen (e.g., diameter: 8 mm, height: 5 mm) may be set on the lower plate of the MTS and compressed by the upper plate connecting to a load cell, with an applied strain rate set at 0.1% per minute at ambient temperature. Fracture stress may be determined from the peak of the stress-strain curve. Initial compressive moduli may be determined from the stress strain profiles.

Biologically, the hydrogels will be nontoxic. Cytotoxicity can be assessed using the MTS cell proliferation assay. The hydrogels can also have the capacity to support cell adherence, growth, and ECM deposition for a period of at least or about 7 days to one month (i.e., 30 days).

To evaluate the cytotoxicity of a hydrogel, a hydrogel can be cultured in the presence of a biological cell for a period of at least one day and for as long as 90 days or more. Methods for culturing cells can be found, for example, in Freshney (Freshney, *Culture of Animal Cells: a Manual of Basic Techniques*, Fourth Edition, Wiley-Liss, New York, USA., 1994). Cell viability, which is inversely proportional to cytotoxicity, may be assessed using, for example, the MTS cell viability assay according to the manufacturer's instructions.

To determine whether a hydrogel is biodegradable, a first fracture stress value may be determined for a hydrogel that has not been exposed to a biological environment (e.g., implanted in vivo or exposed to a population of cells (e.g., fibroblasts) or tissue in tissue culture). A second fracture stress value may then be determined for the same hydrogel following exposure to a biological environment for a certain amount of time (e.g., for a time period of at least 7 days to a maximum of 60 days). The first and second fracture stress values may then be compared to identify a change in the fracture stress value. In some embodiments, the first and second fracture stress values will be compared, and the difference of between the second and first fracture stress values will be expressed as a percentage difference.

Methods of treatment: The double network hydrogels described herein can be administered to a subject by standard methods. For example, a double network hydrogel can be administered during invasive or open spine surgery.

The present methods can be used to treat a spinal disorder in a subject in need thereof, and identification of the subject can be an initial step. In general, the methods include administering (e.g., surgically injecting or implanting), a double network hydrogel in a subject. The double network hydrogel may be implanted alone or in combination with an additional spinal device, implant, or pump. Upon administration, the double network hydrogel serves as a load bearing orthopaedic implant, and can be characterized as a spinal disc substitute.

In some embodiments, the double network hydrogel may be surgically implanted within the disc annulus of an existing disc. For example, the present hydrogel can replace the nucleus pulposus of a disc. In other embodiments, the double network hydrogel may replace the disc (i.e., the spinal disc may be completely removed and replaced with a multi- or double network hydrogel). Thus, the double network hydrogels described herein may be used as an intervertebral disc replacement or as a prosthetic nucleus. In some embodiments, multiple double network hydrogels (e.g., 1, 2, 3, 4, and 5) that are equal in size may be implanted to fill a target space, e.g., a space formed by the surgical removal of one or more discs. In some embodiments, the size of a single double network hydrogel will be customized to fill a target space, e.g., a space formed by the surgical removal of one or more discs.

The intervertebral disc replacement and/or the prosthetic nucleus will support the load required of the disc (e.g., a lumbar disc) to be replaced. For example, the compressive load on the third lumbar disc of the human body is 300 newtons (N) when the body is supine and 700 N when the body is upright (U.S. Pat. No. 5,976,186). Thus, an intervertebral disc replacement and/or a prosthetic nucleus at the third lumbar disc will support at least these loads. In some embodiments, a double network hydrogel will be customized to support the compressive load of the target disc or nucleus pulposus to be replaced. The ability of an intervertebral disc replacement and/or a prosthetic nucleus to support the required load can be verified, for example, using the structural and mechanical tests described herein and/or known in the art.

A compressive load may promote gradual changes in the height of the intervertebral disc replacement and/or a prosthetic nucleus may occur (a phenomenon referred to in the art as creep). Thus, the intervertebral disc replacement and/or a prosthetic nucleus will recover some or all of its original height (i.e., its height before loading), when the load in removed. The creep of a double network hydrogel can be customized to match that of the target intervertebral disc or nucleus pulposus to be replaced. For example, the ability of an intervertebral disc replacement and/or a prosthetic nucleus to creep and recover may be controlled by varying the water content of the hydrogel. Methods for determining the equilibrium water content (EWC) of a hydrogel are known in the art and are described below in Example 4. In some embodiments, the water content of the intervertebral disc replacement and/or a prosthetic nucleus can be 70-99%, e.g., 70-95%; 70-90%; and 80-90%.

Similarly, the Poisson's ratio of the present hydrogels can have a Poisson's ratio that is not significantly different from that of the Poisson's ratio of the target intervertebral disc to be replaced. For example, a double network hydrogel may have a Poisson's ratio of between approximately 0.30 to approximately 0.49 (e.g., approximately 0.35 to approximately 0.49). Where the nucleus pulposus is replaced, the double network hydrogel can have a Poisson's ratio that is not significantly different to the Poisson's ratio of the target nucleus pulposus to be replaced. For example a double network hydrogel may have a Poisson's ratio of between approximately 0.3 to approximately 0.8 (e.g., approximately 0.3 to 0.7, 0.3 to 0.6, 0.3 to 0.55, 0.3 to 0.49, or 0.35 to 0.49). The Poisson's ratio of a double network hydrogel can be customized to match the target intervertebral disc or nucleus pulposus to be replaced. In some embodiments, a hydrogel will have a negative Poisson's ratio, e.g., −1 to 0.

One of ordinary skill in the art will appreciate that the exact size and shape of an intervertebral disc replacement and/or a prosthetic nucleus can be varied for different individuals. For example, the typical dimensions of an adult nucleus is 2 cm in the semi-minor axis, 4 cm in the semi-major axis, and 1.2 cm in thickness (U.S. Pat. No. 5,976,186). The exact size and shape of intervertebral disc replacement and/or a prosthetic nucleus required for a specific subject can be determined by a clinician based on, for example medical images, or measurements taken during surgery.

The present double network hydrogels may be used to make an intervertebral disc replacement and/or a prosthetic nucleus by casting the hydrogel in a mold. The resulting double network hydrogel can then be directly implanted in a subject as an intervertebral disc replacement and/or a prosthetic nucleus.

The double network hydrogel may be dehydrated before implantation. Dehydrated hydrogels are, in general, 50-90% smaller than their hydrated form and thus may be easier to implant in a subject. Dehydrated double network hydrogels may be implanted into a subject, and subsequently rehydrated to sufficiently occupy a desired space. In other embodiments, the double network hydrogel may be prepared or supplied in a size larger than the size of the double network hydrogel to be implanted into a subject. This double network hydrogel may then be cut to the required size using a lathe. Both hydrated and dehydrated double network hydrogels may be cut to size. However, the size of a dehydrated hydrogel following rehydration should be taken into consideration before cutting.

One of skill in the art can implant hydrated or dehydrated double network hydrogels of the present invention into a subject using standard, surgical techniques or procedures well known in the art. In some embodiments, the surgical procedures will be invasive. In some embodiments, the surgical procedures will be marginally invasive. In some embodiments, the surgical procedures will be minimally invasive.

In some embodiments, implantation of double network hydrogel will first require the removal of the disc to be replaced. Methods for the removal of a spinal disc, a discectomy, and other procedures for spinal surgeries are described, for example, in U.S. Pat. Nos. Re. 33,258, 4,573,448, 5,015,255, 5,313,962, 5,383,884, 5,702,454, 5,762,629, 5,976,146, 6,095,149, 6,127,597, and 7,014,633.

Implantation of a double network hydrogel may not require removal of the disc. As noted above, a double network hydrogel may be used to replace the nucleus pulposus of a disc. A method and device for implanting a prosthetic nucleus is described in U.S. Pat. No. 7,204,851. In some embodiments, methods for implanting a prosthetic nucleus may involve (a) making a hole in the annulus of a disc, with the hole having an undilated size that is smaller than the cross-sectional size of the hydrogel in a hydrated state; (b) using an implant instrument to dilate the hole in the disc annulus; (c) using the implant instrument to pass a dehydrated double network hydrogel through the dilated hole and into the disc nucleus space; (d) withdrawing the implant instrument and allowing the hole in the disc annulus to return to a size smaller that its dilated size; and (e) causing or allowing the double network hydrogel to increase in size such that the double network hydrogel occupies the disc nucleus space. This method may further comprise removing the nucleus pulposus prior to implanting the double network hydrogel.

In some embodiments, the double network hydrogel may be injected into a disc using an intradiscal injection. This may be achieved by injecting the first and second network into the disc nucleus space. The first and second networks may be administered together, e.g., from a mixed solution, or within a period of less than one hour. The first and second networks may also be administered separately. Irrespective of the administration method, the double network will then be allowed to form within the intradiscal space.

In some embodiments, in situ gelable double network hydrogel may be injected into the disc nucleus space.

In some embodiments, the invention provide methods to determine the structural, mechanical, and/or biological characteristics required for a specific load bearing application, and methods for manipulating the structural, mechanical, and/or biological properties of a double network hydrogel by varying the concentration of the hydrophilic polymer and/or the crosslinker in the second network to obtain a double network hydrogel with the determined structural, mechanical, and/or biological characteristics.

In some embodiments the double network hydrogel may comprise a bioactive agent, a biological cell, one or more components of the ECM (e.g., collagen), and one or more chemoattractants. In some embodiments, the bioactive agent may be a pharmaceutical agent selected from the group consisting of a therapeutic antibody, an analgesic, an anti-viral agent, an anti-inflammatory agent, an RNA that mediates RNA interference (e.g., a small inhibitory RNA, a short hairpin RNA (shRNA), and an antisense oligonucleotide), a micro RNA, an aptmer, a peptide or peptidomimetic, or an immunosuppressant.

Spinal disorders that may be treated using the compositions and methods of the present invention include, but are not limited to, disk disorders, disorders of spinal stability, disorders of the vertebrae including kyphosis and facet joint disease, arthritic spinal disorders, back pain conditions, and failed back surgery syndrome (FBSS). In one aspect, a disk disorder may be a herniated disk or a degenerative disk disorder. In a further aspect, a disk disorder may be selected from the following group: prolapsed disk, protruding disk, extruded disk, bulging disk, sequestered disk, DDD, DDD with internal disk derangement, diskogenic pain, annular disorder, annular bulge, annular tear, nucleus pulposus degeneration, NR compression, radicular pain, radiculopathy, sciatica, radiating pain, and distraction injury. A disorder of spinal stability may be selected from the following group: spondylolysis, spondylolisthesis, lytic spondylolisthesis, degenerative spondylolisthesis, lumbar spondylolisthesis, isthmic spondylolisthesis, and grade 1 spondylolisthesis. Vertebral disorders that may be treated using the methods disclosed herein may be selected from the following group: vertebral body collapse, vertebral body degeneration, vertebral body compression, metastasis, kyphosis, facet joint disease, facet disease, facet joint disease facet joint syndrome, and impinging facet joints. Arthritic spinal disorders that may be treated using the methods disclosed herein may be selected from the following group: rheumatoid arthritis, ankylosing spondylitis, osteoarthritis, degenerative spinal arthritis, cervical arthritis, thoracic arthritis, DDD, bone spurs, osteophytes, and an arthritic facet joint disorder.

Patient Selection: The methods described herein include methods for identifying a subject with a spinal disorder, and administering to the subject a double network hydrogel. A subject in need of treatment with the methods described herein may be identified by a clinician, a spine specialist, or a spine surgeon as a subject in need of an invasive spinal procedure to treat a spinal disorder or that may benefit from an invasive spinal procedure.

Dual Network Hydrogel Formulations: The dual network hydrogels described herein may be suitable for administration to a subject, e.g., a human. In some embodiments, the double network hydrogels may include, either as part of the double network hydrogel or as part of a solution used to store the double network hydrogels, the following components: water; saline solution; oils; glycerine; antibacterial agents such as benzyl alcohol or methyl parabens; antioxidants such as ascorbic acid or sodium bisulfite; chelating agents such as ethylenediamineteraacetic acid; buffers such as acetates, citrates, or phosphates. The pH of the double network hydrogels and or the storage solution may be adjusted with acids or bases, such as hydrocholoric acid or sodium hydroxide. In all cases, the double network hydrogels and storage solutions must be sterile, stable under the conditions of manufacture and storage, and preserved against the contaminating action of microorganisms such as bacteria and fungi. Sterility can be achieved, for example, by filter sterilizing each component of the double network hydrogels, prior to production of the hydrogel, and each component of the storage solution.

Intervertebral Discs and Kits: The invention features a kit containing the double network hydrogel intended for use in any of the aforementioned features. Kits may contain the invention in a pre-made state or individual components thereof to be prepared prior to use. The specific components and compositions of the kits may vary depending on a subject's requirements. For example, in some embodiments, the size and/or mechanical properties of the double network hydrogel may vary. In some embodiments, the ratios and/or volumes of the first and second network supplied to prepare a double network hydrogel prior to use may vary.

In some embodiments, a kit can contain one or more of the following components in a package or container: (1) a pre-made double network hydrogel or a composition comprising a first network that is stiff and brittle and a composition comprising a second network that is soft and ductile; (2) one or more additional spinal devices or implants; (3) tools to implants the double network hydrogel and components of (2); (4) one or more of the following a bioactive agent, a biological cell, components of the ECM (e.g., collagen), and a chemoattractant; and (5) instructions for administration. Embodiments in which two or more, including all, of the components (1)-(5) are found in the same container can also be used.

When a kit is supplied, the different components of the compositions included can be packaged in separate containers and admixed immediately before use. Such packaging of the components separately can permit long term storage without compromising the characteristics or functions of the components. When more than one bioactive agent is included in a particular kit, the bioactive agents may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on a internet web site or may be distributed to the user as an electronic mail.

EXAMPLES

The invention is further described in the following non-limiting examples.

Example 1

Preparation of Photocrosslinkable Ha

Photocrosslinkable HA was prepared by derivatizing commercially available sodium HA ($M_w$ 1.5×10$^6$) with methacrylate (Leach et al., *Biotech. Bioeng.*, 82:578-579, 2003), as follows. First, a 1% g/mL HA solution was prepared in water. Second, 20 mol-% triethylamine (relative to the total hydroxyls on HA), 20 mol % tetrabutylammonium bromide (TBAB), and a 20-fold excess of glycidyl methacrylate (GMA) were added separately to the HA solution and thoroughly mixed. Third, the reaction was incubated for 2 hours at room temperature to allow trans-esterification of the HA and GMA. Fourth, the reaction mixture was dialyzed extensively against 0.1 M NaCl followed by water. Fifth, the solution was lyophilized and the resulting photocrosslinkable HA was recovered. Finally, the substitution degree of HA was determined by $^1$H-NMR (Varian Unity-500, CA, USA). Sodium HA was supplied by BASF (Stony Brook, N.Y.). Triethylamine, TBAB, and GMA were supplied by Sigma-Aldrich Co. (St. Louis, Mo.).

As shown in FIG. 1, $^1$H-NMR revealed two unique peaks at about 5.6 and about 6.1 ppm for photocrosslinkable HA. These peaks were attributed to the presence of acrylate groups on HA. This observation confirms the grafting of methyacrylate groups onto HA chains.

Percentage methylation was determined by integrating the methyl peak observed at 1.9 ppm with the acrylic double bond peaks. The result suggested that the above described technique resulted in approximately 10% modification of HA.

These results demonstrate that HA can be successfully modified using GMA to produce methyacrylated HA. This modified form of HA is suitable for photocrosslinking.

Example 2

Photocrosslinking Photocrosslinkable HA

The photocrosslinkable HA described in Example 1 was photocrosslinked by irradiating a 2% (w/v) photocrosslinkable HA solution with UV light at 365 nm for 2 hours in the presence of the photoinitiator 2-oxo-ketoglutaric acid at a concentration of 0.1 mol-%. The resulting photocrosslinked HA hydrogel was designated PHA.

Example 3

Preparation of Double Network Hydrogels

A series of double network hydrogels were prepared by contacting PHA with varying amounts of the monomer of the hydrophilic synthetic polymer poly(N,N-dimethylacrylamide) (PDMAAm), i.e., N,N-dimethylacrylamide (DAAm), in the presence of the crosslinking agent N,N'-methylene bisacrylamide (MBAAm) and the photoinitiator 2-oxo-ketoglutaric acid. Double network PHA and DAAm hydrogels were designated PHA/DAAM hydrogels.

Multiple PHA/DAAm hydrogels were prepared with incremental properties, as follows. For a typical preparation, a PHA hydrogel was immersed in a DAAm solution at ambient temperature. The concentrations of DAAm monomers used were 1-5 mol/L (i.e., 1, 2, 3, 4, and 5 mol/L). These solutions also contained various amounts of MBAAm crosslinker ranging from 0-2 mol-% with respect to the DAAm monomer concentration (i.e., 0, 0.01, 0.05, 0.1, 0.5, 1, and 2 mol-%), and 0.1 mol-% 2-oxo-ketoglutaric acid. The amounts and combinations of DAAm and MBAAm were varied until equilibrium was reached. Equilibrium was determined by observing the weight changes of the hydrogel. The PHA hydrogel and DAAm solution were then irradiated for 2 hours under UV light at 365 nm. DAAm and MBAAm were supplied by Sigma-Aldrich Co.

To distinguish between different PHA/DAAm hydrogels, a nomenclature was developed in which each hydrogel was designated according to the concentration of the monomer (DAAm) and the crosslinker (MBAAm) used in the preparation of the respective PHA/DAAm hydrogel. Thus, PHA/DAAm hydrogels were designated PHA/D-x-y hydrogels; where "x" is the monomer concentration and "y" is the crosslinker concentration. For example, a hydrogel formulated from a PHA network combined with 3 mol/L DAAm, 0.01 mol-% MBAAm and 0.1 mol-% 2-oxoglutaric acid, was designated PHA/D-3-0.01. The amount of PHA hydrogel used in the preparation of each of these exemplary hydrogels was constant.

PHA, PHA/D-3-0.01, PHA/D-3-0.05, and PHA/D-3-2 hydrogels were analyzed using scanning electronic microscopy (SEM), as follows.

PHA/DAAM hydrogels were snap frozen in a glass container using liquid nitrogen followed by lyophilization. Fractured pieces of hydrogel with size of about 5 mm×2 mm×3 mm were mounted onto an aluminum board with copper tapes and coated with gold by plasma vapor deposition. The surface and cross-sections were examined with a field-emission scanning electron microscope (SFEG Leo 1550, AMO GmbH, Aachen, Germany) at 20 kV.

Figures 2A, 2B, 2C, 2D:
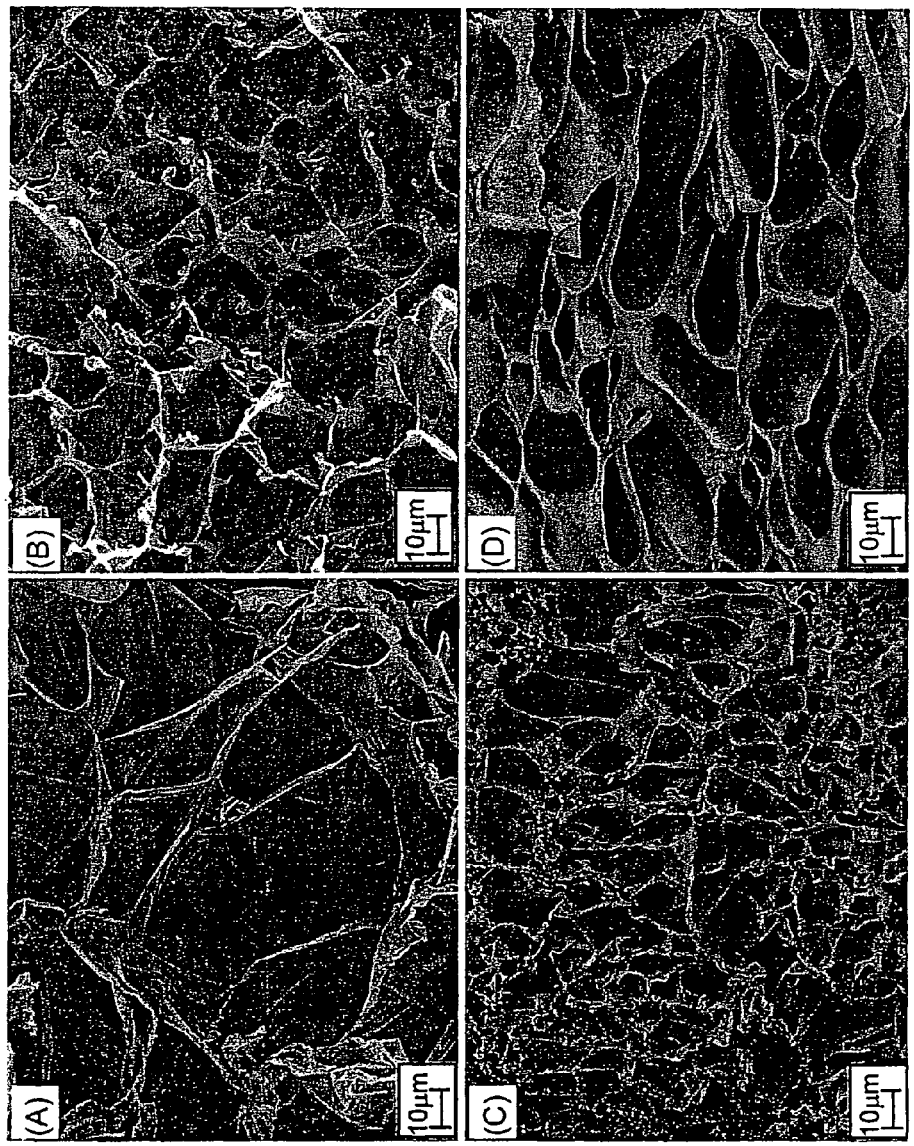
FIGS. 2A-2D are representative scanning electronic microscopy (SEM) images for lyophilized PHA (A), PHA/D-3-0.01 (B), PHA/D-3-0.05 (C), and PHA/D-3-2 (D) hydrogels. Scale bar: 10 μm.

As shown in FIG. 2, of the four hydrogels analyzed using SEM, pure PHA hydrogel exhibited the largest pore size (on average, 50 μm). The other three hydrogels PHA/D-3-0.01, PHA/D-3-0.05, and PHA/D-3-2 appeared to have more compact porous structures with an average pore size ranging from 10 to 20 μm. This is due to the presence of the second PDAAm network, which increased the relative crosslinking density of the hydrogel structure. The pore partitions of PHA/D-3-2 hydrogel were the thickest.

These results demonstrate that a double network hydrogel can be formed using the techniques described above. This double network hydrogel has physical properties that are distinct from its parent single network HA hydrogel.

Example 4

Physical Characterization of Double Network Hydrogels

Equilibrium swelling studies were performed on multiple PHA/DAAM hydrogels. Lyophilized hydrogels were first weighed ($W_d$) and immersed in 0.01 M PBS at 37° C. Following five days of equilibration, the hydrogels were removed from the PBS solution, blotted with tissue for removal of excess water, and weighed for a second time ($W_s$). Equilibrium water uptake studies were also performed on both single network PHA and PDAAm hydrogels, respectively.

The equilibrium water content (EWC) was calculated through the following equation:

$$EWC(\%) = 100(W_s - W_d)/W_s.$$

Figures 3A, 3B:
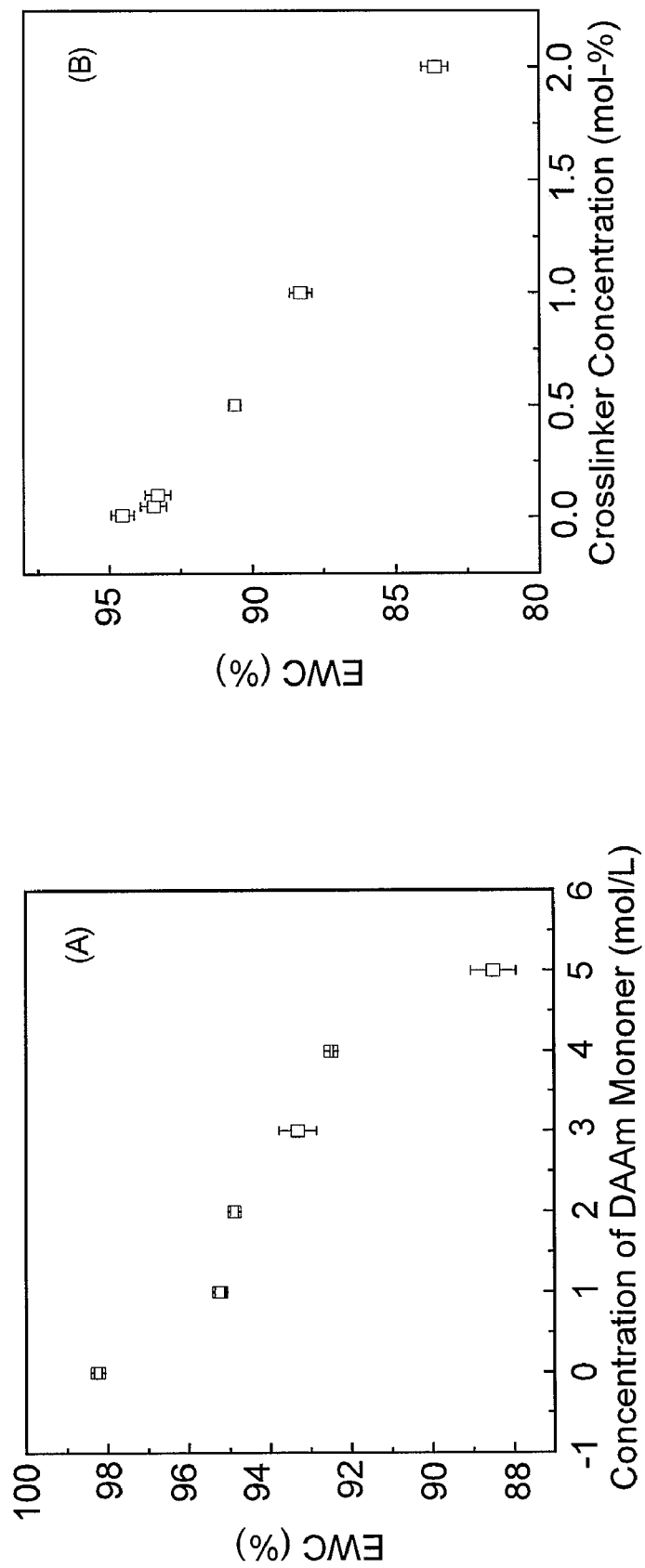
FIGS. 3A-3B are line graphs showing the variation of hydrogel equilibrium water content (EWC) with varying DAAm monomer (A) and MBAAm crosslinker (B) concentration.

As shown in FIGS. 3A and 3B, EWC values greater than 80% were observed for all hydrogels. As shown in FIG. 3A, the EWC of the PHA hydrogel (i.e., DAAm monomer concentration=0 mol/L), was approximately 98%. Introduction of the second network and formation of a PHA/DAAM caused a decrease in EWC values of approximately 98% to 88%. This observation correlated with the increased crosslinking density, noted in FIG. 2, caused by a corresponding increase of the DAAm monomer concentration from 0 to 5 mol/L, while maintaining the crosslinker concentration at 0.1 mol-%.

As shown in FIG. 3B, EWC also depended on the concentration of the crosslinker (MBAAm) used in the second network. A decrease in EWC was observed with an increase in the concentration of crosslinker in the second network. For example, when the concentration of DAAm monomer was kept at 3 M, an increase in MBAAm concentration from 0.01 mol-% to 2 mol-% reduced the EWC from 94% to 83%. Higher crosslinker concentration created a denser polymer network, likely causing the polymeric chains to move in closer proximity to each other, which enabled stronger hydrophobic interactions, leading to lower EWC.

These results demonstrate that double network hydrogels possess porous internal structures with good swelling properties. These properties are related to the concentration of the DAAm monomer and the concentration of the MBAAm crosslinker. Thus, double network hydrogel formulations may be easily modified to control the physical properties of the double network hydrogel produced.

Example 5

Mechanical Characterization of Multiple Double Network Hydrogels

Mechanical evaluations were ideally performed on fully hydrated hydrogels devoid of air bubbles and other obvious or immediately apparent physical imperfections.

Mechanical properties of the swollen hydrogels were performed using an MTS mechanical tester (Model 1K-16 Universal Materials Tester, Interactive Instruments, USA), as follows. A cylindrical hydrogel specimen (diameter: 8 mm, height: 5 mm) was set on the lower plate and compressed by the upper plate connecting to a load cell, with an applied strain rate set at 0.1% per minute at ambient temperature. The initial compressive modulus was determined by the average slope in a range of 0-10% strain from the stress-strain curve. The fracture stress was determined from the peak of the stress-strain curve.

Figure 4:
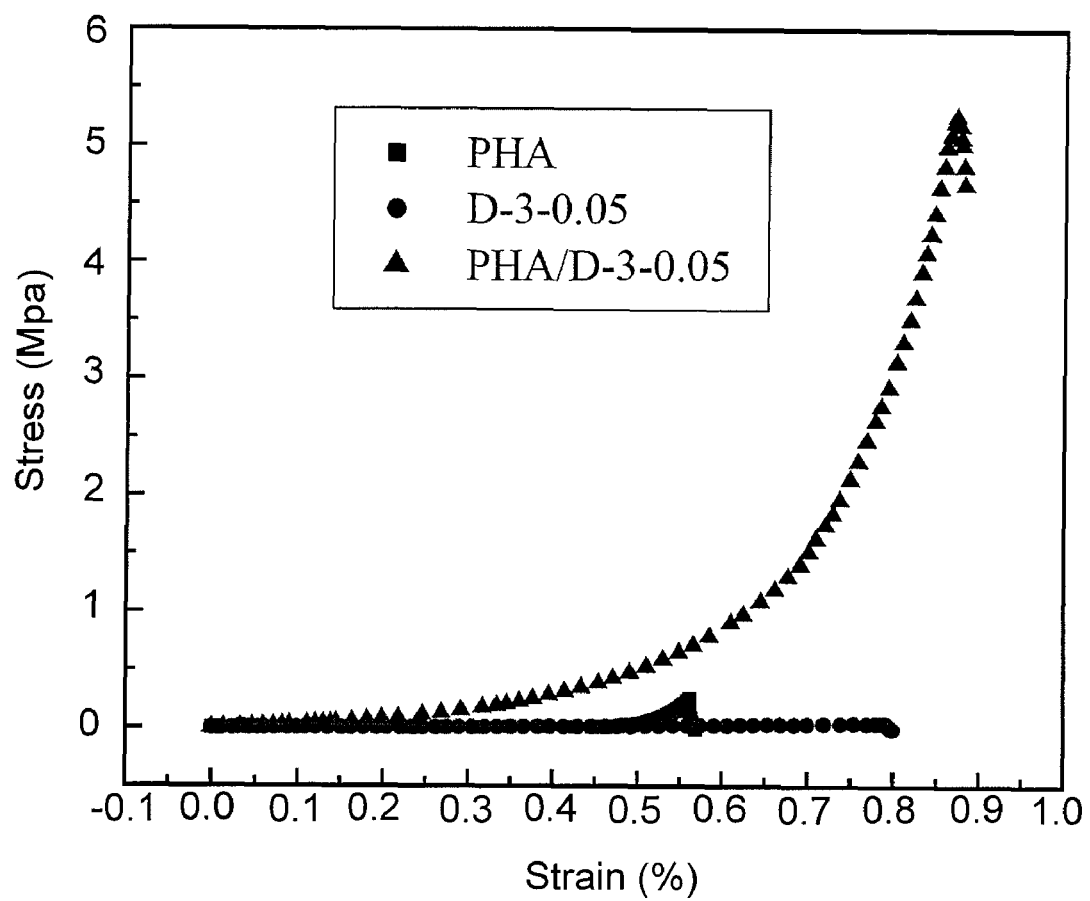
FIG. 4 is a line graph showing stress-strain profiles for the PHA, PHA/D-3-0.05 and P-3-0.05 hydrogels under uniaxial compression.

As shown in FIG. 4, PHA and D-3-0.05 single network hydrogels fractured at the stresses 0.29 MPa and 0.04 MPa, respectively, while the PHA/D-3-0.05 possessed a fracture stress of over 5.25 MPa. The fracture strain of PHA/D-3-0.05 hydrogel was 87.1%, which was considerably higher than that of either the PHA (56.1%) hydrogel or the D-3-0.05 (78.4%) hydrogel. The mechanical effect produced by a double network structure suggested that one of the networks contributed to the elastic stress, whilst the other one contributed to the strain.

The stress-strain profiles obtained suggested that the PHA hydrogel was brittle whilst the D-3-0.05 hydrogel was more ductile. These results suggest that the brittle PHA network of PHA/D-3-0.05 contributed to the elastic stress and the D-3-0.05 network contributed to the strain of the double network hydrogel.

The initial compressive moduli of hydrogels were deduced from the stress-strain profiles. All PHA/DAAm hydrogels showed similar initial compressive moduli in the magnitude of $10^{-1}$ MPa. Representative results of the initial compressive moduli of PHA, PHA/D-3-0.01, PHA/D-3-0.05, and PHA/D-3-2 hydrogels are summarized in Table 1. With the exception of the PHA hydrogel possessing a relatively low compressive modulus at 0.045 MPa, the other three hydrogels exhibited comparable moduli in the range of 0.3-0.6 MPa.

TABLE 1

Initial Compressive Modulus of Hydrogels

| Elastic Modulus (MPa) | PHA | PHA/ D-3-0.01 | PHA/ D-3-0.05 | PHA/D-3-2 |
|---|---|---|---|---|
| Without Cells | 0.045 ± 0.005 | 0.397 ± 0.07 | 0.508 ± 008 | 0.442 ± 0.11 |
| With Cells | 0.037 ± 0.006 | 0.260 ± 0.06 | 0.246 ± 0.03 | 0.235 ± 0.05 |

These results suggest that (1) the molar ratio of the second network to the first network and (2) the crosslinking density of the second network affect the structural parameters of the double network hydrogels described herein. These parameters should be optimized in order to obtain a first network with a stiff and brittle state and a second network that is soft and ductile.

As described in Example 3, double network hydrogels were prepare using 1-5 mol/L, e.g., 3 mol/L DAAm. The optimal concentration of DAAm for achieving the highest mechanical strength for PHA/DAAm hydrogels with a crosslinker concentration of 0.1% was 3 mol/L. To further examine the effect of crosslinker concentration on the mechanical properties of the PHA/DAAm hydrogels, the crosslinker concentration was varied while the DAAm concentration remained constant (3 mol/L).

Figures 5A, 5B:
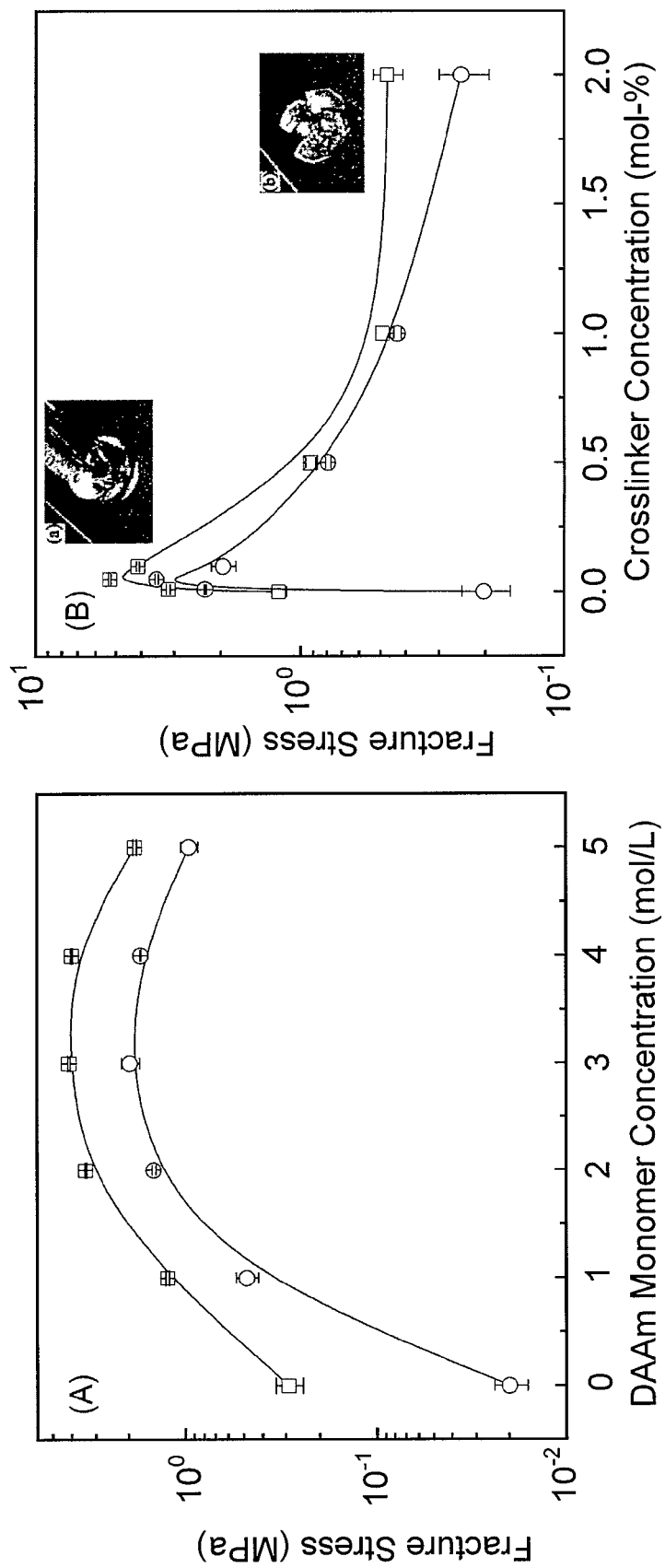
FIGS. 5A-5B are line graphs showing the effect of (A) monomer concentration and (B) crosslinker concentration on the fracture stress of hydrogels in the absence of cells (squares) or following co-culture of the hydrogels with cells for two-months (circle).

As shown in FIG. 5B, a maximal fracture stress value of 5.25 MPa was attained using a crosslinker concentration of 0.05 mol-% (e.g., PHA/D-3-0.05). In addition, no specific interactions, such as phase separation or strong molecular interactions, were observed for this formulation. Furthermore, this abrupt increase in mechanical strength was not due to increased chemical crosslinkage or physical entanglement since the second network was loosely crosslinked.

The highly crosslinked first network has a relatively higher modulus but is rather brittle. Therefore, under compression, stress could easily develop locally inside the network, leading to the formation of cracks. However, the presence of the soft but loosely crosslinked second network could effectively dissipate the stress imposed during compression by deforming the network conformation and/or sliding the physical entanglement points along the polymer chains.

As shown in FIG. 5B, increasing the crosslinker concentration from 0.05 to 2 mol-% resulted in a progressive decrease of fracture stress of the hydrogels. This increase in the crosslinker concentration resulted in substantial increase in the crosslinking density and thus, formation of a stiffer network with very limited capacity to dissipate stress imposed during compression, leading to the reversal of the double network effect.

In FIG. 4B, the water content of the PHA/DAAm hydrogel formulated from 3 mol/L of DAAm with a 0.05 mol-% crosslinker concentration was greater than 93%. In general, when hydrogels are fully swollen, their compressive fracture stresses are lowered due to the softer network. The prior art suggests that HA-based hydrogels should not swell significantly after curing, as this may affect the mechanical properties of the hydrogels (Park et al., *Biomaterials*, 24:893-900, 2003). Based on these teachings, it was surprising that the fully swollen PHA/D-3-0.05 hydrogel still possessed a high fracture stress at 5.25 MPa, implying that the double network effect could greatly improve the mechanical strength of the swollen hydrogels. Moreover, as shown in FIG. 5A, all the dual network hydrogels examined exhibited one definitive fracture line when broken. This pattern was distinctively different from hydrogels composed of a single network or interpenetrating polymer networks without the dual network effect, which tended to fracture into multiple fragments under compression (compare FIGS. 5A and 5B).

These results suggest that the structural and mechanical properties of the PHA/DAAm hydrogels described herein do not deteriorate over time.

Example 6

Biodegradation of Double Network Hydrogels

Double network hydrogels were co-cultured with M. DUNNI murine dermal fibroblast CRL-2017 cells (ATCC, Manassas, Va.). Cells were cultured in McCoy's 5A medium (ATCC) supplemented with 10% fetal bovine serum (FBS; Hyclone, Utah) and 1% penicllin-streptomycin (Gibco, N.Y.) at 37° C. in a humidified atmosphere of 5% $CO_2$. Cells were cultured using polycarbonate cell culture inserts supplied by NUNC (Rochester, N.Y.) with a 6.5 mm diameter and 0.2 µm pore size, as follows. Briefly, hydrogel cylinders (diameter: 8 mm, height: 5 mm) were deposited in 24 well plates, and $1 \times 10^6$ cells were seeded in each well. Culture medium was changed every other day. Cells were cultured for 2 months before the hydrogel cylinders were retrieved and fixed with 70% ethanol. Hydrogels were then rinsed three times with PBS. All hydrogels were maintained in PBS for mechanical testing.

The compressive moduli of the hydrogels after 2 month of cell culture is presented in Table 1. Fibroblasts secrete a myriad of hydrolases, including hyaluronidase (Hornebeck et al., *Pathol. Biol.*, 51:569-573, 2003), which is capable of degrading the PHA network despite photocrosslinking. As shown in Table 1, the moduli of PHA and PHA/DAAm hydrogels all declined after 2 months, with a comparable final moduli for all formulations (the single network PHA hydrogel as the control).

As shown in FIG. 5A, the fracture stress of PHA single network hydrogels decreased drastically from 0.29 MPa to 0.019 MPa, whereas the fracture stress of PHA/DAAm hydrogels were only moderately reduced by cell-mediated degradation. Furthermore, as shown in FIG. 5B, the peak value (i.e., the double network effect) was maintained at a crosslinker concentration of 0.05 mol-%. Therefore, hydrogels with higher DAAm or MBAAm concentrations exhibited less decrease in failure stress.

After prolonged co-culturing with cells, gross observation revealed no noticeable changes for the hydrogel specimens cultured with cells when compared to their pristine counterparts that were not exposed to cells. This observation suggests that the stable bonds formed using the free radical polymerization technique described in Example 3 are highly resistant to biodegradation. This feature may be attributed to the poly (N,N-dimethylacrylamide), which is not biodegradable.

These results suggest that PHA/DAAm double network hydrogels are not susceptible to biodegradation and, therefore, may be useful as long-term implantables.

The results presented in Examples 4-6 demonstrate that double network hydrogels comprising HA and poly(N,N-dimethylacrylamide) and prepared using a two-step photocrosslinking process exhibit porous internal structures with good swelling and mechanical properties. These properties were not observed for single network HA based hydrogels. Such useful mechanical properties include the high mechanical strength of the hydrogel, which can be attributed to ability of the loosely crosslinked second network to dissipate stress during compression. Furthermore, the mechanical properties of these PHA/DAAm double network hydrogels can be manipulated by varying the DAAm monomer concentration of the second network, or the crosslinker concentration of the second network, or both. Thus, it is conceivable that PHA/DAAm double network hydrogels could be adapted for different applications, for example, applications requiring more or less mechanical strength.

Example 7

Cell Viability Assays

To determine whether the double network PHA/DAAm hydrogels were cytotoxic, M. DUNNI murine dermal fibroblast CRL-2017 cells were cocultured using an indirect contact method, as follows. PHA, PHA/D-3-0.01, PHA/D-3-0.05, and PHA/D-3-2 hydrogels were cocultured in 96-well plates containing $1 \times 10^5$ cells/mL and sterilized 5 mm×2 mm×2 mm pieces of PHA and PHA/DAAM hydrogels. Briefly, each hydrogel was deposited into a cell culture insert, which was suspended immersed in one well of a 96-well plate seeded with $1 \times 10^5$ cells/mL. Cells were cultured as described in Example 6. Cell viability was measured on days 0, 3, 7, 10 and 14 using the MTS cell proliferation assay. For each time point, 20 µL MTS solution was added to the culture medium. The solutions were then incubated for 1 hour at 37° C. for 1 h; absorbance was measured at 490 nm. Cell monolayers cultured in the absence of a hydrogel were used as controls. Using this system, hydrogels could be removed and replaced without disturbing adherent cells. Thus, the same cell population could be assessed at each time point.

Figure 6:
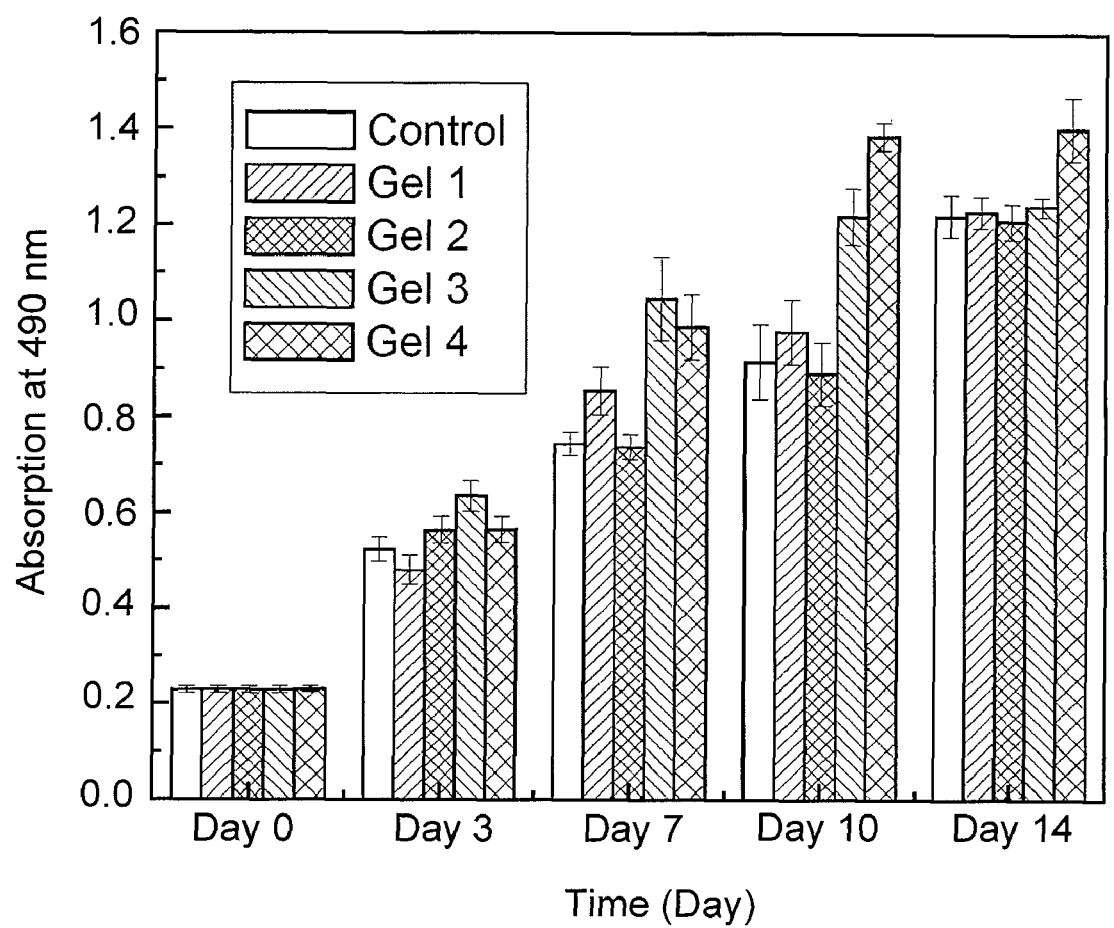
FIG. 6 is a histogram showing cell viability in the presence of HA derivative double network hydrogels; where Gel 1 is PHA/D-3-0.01; Gel 2 is PHA/D-3-2; Gel 3 is PHA/D-3-2; and Gel 4 is PHA. Control cells were cultured in the absence of a hydrogel.

Cell morphology and number did not vary in any of the samples during the course of this experiment (14 days). As shown in FIG. 6, as assessed by an increase in absorption at 490 nm, a similar increase in cell proliferation was observed for all groups, including the control, throughout the duration of this study. Moreover, varying the concentration of either DAAm monomer (from 0-3 mol/L) or the crosslinker (from 0.01-2 mol-%) did not effect cell growth.

These data suggests that PHA/DAAm hydrogels do not affect cell viability and growth.

Example 8

Long-Term Coculture Assays and Extracellular Matrix Deposits

Pieces of PHA; PHA/D-3-0.01; PHA/D-3-0.05; and PHA/D-3-2 hydrogels approximately 6 mm×6 mm×1 mm were deposited per well of a 48-well plate. $1 \times 10^5$ M. DUNNI murine dermal fibroblast CRL-2017 cells were then seeded in direct contact with the hydrogels. Cells were cultured as described in Example 6, and the cell culture medium was changed every other day. Images of cells on the surfaces of hydrogels were then captured using QCapture 5 imaging software (Surrey, Canada).

Extracellular matrix (ECM) deposition on the surfaces of the hydrogels was assessed following 2 months of continuous culture. Briefly, hydrogels were recovered and fixed in 70% ethanol for 30 minutes. Fixed hydrogels were then thoroughly rinsed in PBS and finally distilled water to remove residual ethanol. ECM deposition was evaluated by staining fixed hydrogels with Picrosirius Red (0.1% Sirius Red in saturated picric acid), as previously described (Whittaker et al., *Basic Res. Cardiol.*, 89:397-410, 1994); images were captured using standard light microscopy. Under these conditions, hydrogel is yellow and ECM deposits are red. Images of the same regions of the hydrogels' surfaces were also captured using polarized light to evaluate collagen deposition. Under these conditions, collagen in the extracellular matrix is bright red, yellow, and the other components within the ECM and the hydrogel are dark. SEM was also performed using hydrogels prepared as described above and lyophilized.

Figures 7A, 7B, 7C, 7D, 7E, 7F, 7G, 7H:
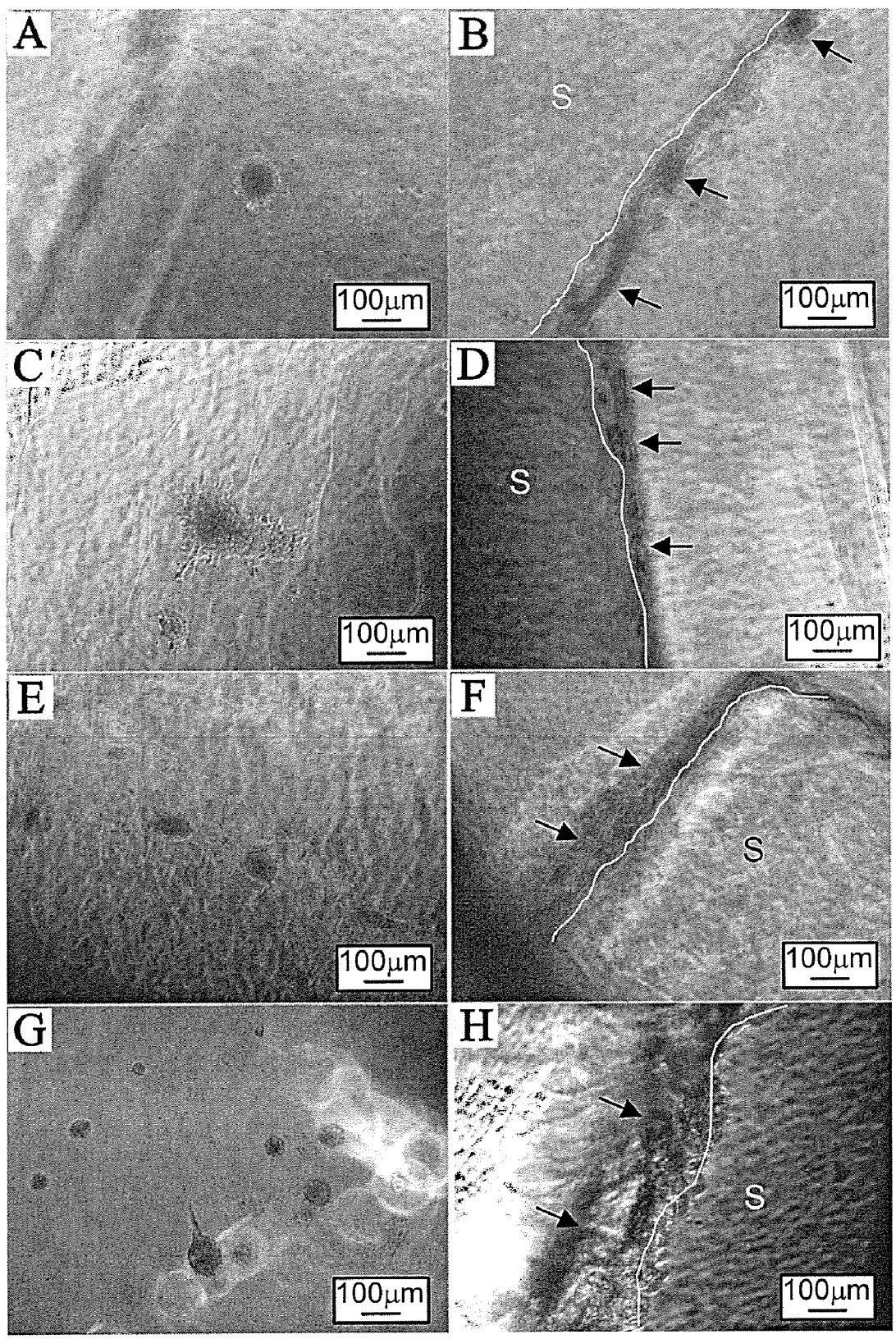
FIGS. 7A-7H are images of cells on the surface (A, C, E, and G) and en face side (B, D, F, and H) of PHA/D-3-0.01 (A-B); PHA/D-3-0.05 (D); PHA/D-3-2 (E-F); and PHA (G-H) hydrogels. (S) indicates a hydrogel surface. Arrow indicates cell clusters on the en face side of a hydrogel. Scale is 100 μm.

As shown in FIG. 7, cells initially clustered, presented round morphologies, and weakly adhered to the hydrogels, indicating that the hydrogel surfaces were poorly conducive to cell attachment. These observations were supported by previous publications, which reported that HA, and PDAAm were unsuitable surfaces for cell attachment (Shu et al., *Biomaterials*, 24:3825-3834, 2003; Tamada et al., *J. Biomed. Mater. Res.*, 28:783-789, 2004; Ramamurthi et al., *J. Biomed. Mater. Res.*, 60:196-205, 2004).

Spreading of fibroblasts on polymer surfaces is dependent on the polar surface free energy, and the extent of cell spreading is low when the polar surface free energy is less than 5 erg/cm2 (Van der Valk et al., *J. Biomed. Res.*, 17:807-817, 1983). The low polar surface free energy of the hydrogel surface may, therefore, account for the observed poor cell spreading. As shown in FIGS. 7B, 7D, 7F and 7H, surprisingly, fibroblasts readily attached to the en face side of the hydrogel (see FIG. 7B, D, F, H) and formed clusters similar to that on the hydrogel surface.

Using light and polarizing light microscopy, collagen deposits were observed on the hydrogel surfaces. These deposits were predominantly Type I collagen and no noticeable differences in collagen compositions were observed for the different hydrogel compositions. These observations demonstrated that despite the initial lack of attachment, fibroblasts gradually produced and deposited ECM on the surfaces of the hydrogels.

Figures 8A, 8B, 8C:
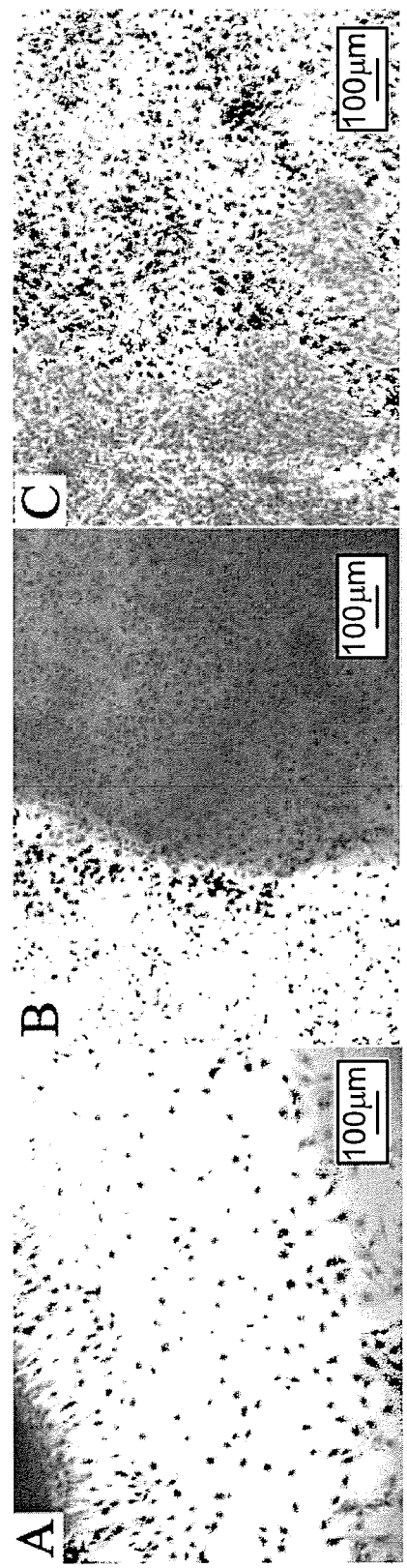
FIGS. 8A-8C are images of cells on the well bottom and underneath the PHA/D-3-0.05 hydrogel after (A) 1 week, (B) 2 weeks, and (C) 1 month. (B) was captured without removing the hydrogel from the well. Cells attached to the surface of the well are shown on the left of the image; cells attached to the hydrogel are shown on the right of the image. Scale is 100 μm.

As shown in FIGS. 8A, 8B, and 8C, after one week, 2 weeks, and one month of incubation, respectively, no morphological differences between fibroblasts residing underneath the hydrogel or on the culture dish (left side, FIG. 9B) were observed. In addition, cells continued to proliferate for periods of greater than 1 month. These results suggest that PHA/DAAm hydrogels are suitable for the long-term culture of cells.

Figures 9A, 9B, 9C, 9D, 9E, 9F:
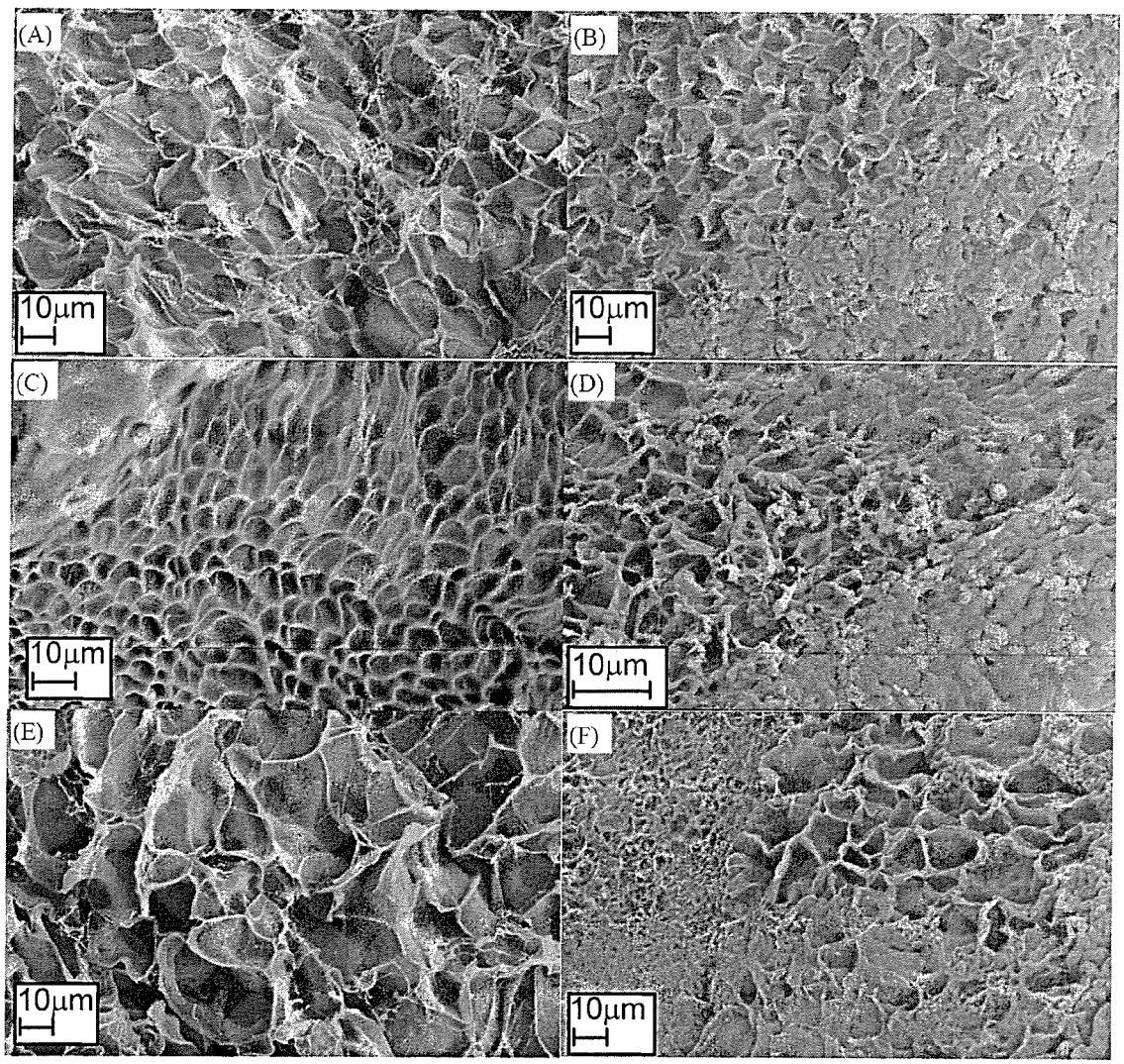
FIGS. 9A-9F are SEM images showing ECM deposition on the surface of PHA/D-3-0.01 (A-B); PHA/D-3-0.05 (C-D), and PHA/D-3-2 (E-F) hydrogels.

As shown in FIG. 9, uneven surface morphologies were observed for pristine hydrogels (i.e., never co-cultured with cells). These surface were generally filled with multiple holes (FIG. 10A) or crumples (FIGS. 10C and 10E). As shown in FIGS. 9B, 9D, and 9F, after 1 month of co-culture with fibroblasts, ECM was observed on the surfaces of the hydrogels. In fact, in FIG. 9B the surface of the hydrogel was nearly completely covered by ECM. As shown in FIGS. 9D, and 9F, surfaces not covered by ECM maintain the structural characteristics.

These results suggest that PDA/DAAm double network hydrogels have great potential for load bearing biomedical applications such as spinal disc substitute.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A hydrogel comprising (a) a first network comprising photocrosslinkable hyaluronan and (b) a second network comprising a hydrophillic polymer or a monomer thereof, wherein (a) and (b) are combined and photocrosslinked.

2. The hydrogel of claim 1, wherein the photocrosslinkable hyaluronan comprises hyaluronan derivatized with glycidyl methacrylate.

3. The hydrogel of claim 2, wherein the hydrogel further comprises a crosslinker and a photoinitiator.

4. The hydrogel of claim 3, wherein the crosslinker is an acrylamide.

5. The hydrogel of claim 4, wherein the acrylamide is N,N'-methylene bisacrylamide (MBAAm).

6. The hydrogel of claim 1, wherein the hydrophilic polymer is a synthetic polymer.

7. The hydrogel of claim 6, wherein the synthetic polymer is an acrylamide.

8. The hydrogel of claim 7, wherein the acrylamide is selected from the group consisting of poly(N,N-dimethylacrylamide) (PDMAAm) or a monomer thereof; 2-N-Acetyl-β-D-glucosamine polyacrylamide biotin or a monomer thereof, α-D-6-O-Phosphomannopyranoside polyacrylamide biotin or a monomer thereof, α-D-Mannopyranoside polyacrylamide biotin or a monomer thereof, aldolase-polyacrylamide or a monomer thereof, biotin-2-N-acetyl-α-D-galactosamine polyacrylamide or a monomer thereof, biotin-α-D-galactopyranoside polyacrylamide or a monomer thereof, biotin-α-D-glucopyranoside polyacrylamide or a monomer thereof, biotin-α-D-N-acetylneuraminide polyacrylamide or a monomer thereof, biotin-β-D-galactopyranoside polyacrylamide or a monomer thereof, biotin-β-D-glucopyranoside polyacrylamide or a monomer thereof, fluorescein-α-D-galactosamine polyacrylamide or a monomer thereof, fluorescein-α-D-mannopyranoside-polyacrylamide or a monomer thereof, fluorescein α-D-N-acetylneuraminide-polyacrylamide or a monomer thereof, fluorescein-β-D-galactopyranoside polyacrylamide or a monomer thereof, fluorescein-β-D-glucopyranoside polyacrylamide or a monomer thereof, fluorescein-β-D-N-acetylgalactosamine polyacrylamide or a monomer thereof, lacto-N-biose polyacrylamide biotin or a monomer thereof, Enzacryl® AA, N,N-dimethylacrylamide or a monomer thereof, poly[N-(1-naphthyl)-N-phenylacrylamide] or a monomer thereof, poly[N-(1-naphthyl)-N-phenylmethacrylamide or a monomer thereof, and 1-[N-[Poly(3-allyloxy-2-hydroxypropyl)]-2-aminoethyl]-2-imidazolidinone or a monomer thereof.

9. The hydrogel of claim 1, wherein the hydrophilic polymer is an organic polymer.

10. The hydrogel of claim 1, further comprising 0-99% water.

11. The hydrogel of claim 1, wherein the hydrogel is lyophilized.

12. The hydrogel of claim 1, wherein the hydrogel has a compressive modulus over about 0.4 MPa and less than about 10 MPa.

13. The hydrogel of claim 1, wherein the hydrogel has a fracture strength of more than about 5.2 MPa and less than about 800 MPa.

14. The hydrogel of claim 1, wherein the crosslinking density of the second network is lower than the crosslinking density of the first network.

15. The hydrogel of claim 1, wherein the second network is present at about 1-5 mol/L.

16. The hydrogel of claim 1, wherein the hydrogel is biocompatible and resistant to biodegradation.

17. The hydrogel of claim 1, further comprising a cell or a component of the extracellular matrix.

18. The hydrogel of claim 1, further comprising a pharmaceutical agent.

19. A medical device comprising the hydrogel of claim 1.

20. The medical device of claim 19, wherein the device is a spinal support device or an artificial vertebral disc.

21. A method for treating a spinal injury or disorder, the method comprising
    (a) identifying a patient in need of treatment; and
    (b) administering to the patient the medical device of claim 20.

22. The method of claim 21, wherein the spinal injury or disorder is a ruptured or injured intervertebral disc or a degenerative disk disease.

23. A method of making a dual network hydrogel, the method comprising:
    (a) providing a photocrosslinked first network comprising hyaluronan;
    (b) providing a second network comprising a organic or synthetic polymer; and
    (c) photocrosslinking the first network and the second network to obtain the dual network hydrogel.

24. The method of claim 23, wherein the photocrosslinked first network is obtained by preparing a solution of hyaluronan in water; adding to the solution triethylamine, tetrabutylammonium bromide and glycidyl methacrylate; dialyzing the solution; lyophilizing the solution; an irradiating the solution in the presence of a photoinitiator.

25. The method of claim 24, wherein the photoinitiator is 2-oxo-ketoglutaric acid.

26. The method of any of claim 23, wherein photocrosslinking the first network and the second network comprises contacting the first network with a hydrophilic polymer or a monomer thereof in the presence of a crosslinking agent and a photoinitiator to create a mixture and subsequently irradiating the mixture.

27. A dual network hydrogel made by the method of claim 23.

28. A kit comprising the hydrogel of claim 1.

* * * * *

UNITED STATES PATENT AND TRADEMARK OFFICE
CERTIFICATE OF CORRECTION

PATENT NO. : 7,763,268 B2  Page 1 of 1
APPLICATION NO. : 12/355577
DATED : July 27, 2010
INVENTOR(S) : Weiliam Chen and Lihui Weng It is certified that error appears in the above-identified patent and that said Letters Patent is hereby corrected as shown below:

Title Page; item (56);

On the First Page, Column 1 (Other Publications), line 5, delete "1505" and insert --150S--

On the First Page, Column 2 (Other Publications), line 9, delete "gelatinechondroitinehyaluronan" and insert --gelatin-chondroitin-hyaluronan--

In Column 21, claim 1, line 4, delete "hydrophillic" and insert --hydrophilic--

In Column 21, claim 8, line 36, delete "fluorescein" and insert --fluorescein- --

In Column 21, claim 8, line 45-46, delete "phenylmethacrylamide" and insert --phenylmethacrylamide]--

Signed and Sealed this

Twenty-third Day of November, 2010

David J. Kappos
*Director of the United States Patent and Trademark Office*